(12) United States Patent
Martin

(10) Patent No.: US 11,858,819 B2
(45) Date of Patent: Jan. 2, 2024

(54) METHODS OF PRODUCING A SYNGAS COMPOSITION

(71) Applicant: Energy and Environmental Research Center Foundation, Grand Forks, ND (US)

(72) Inventor: Christopher Lee Martin, Grand Forks, ND (US)

(73) Assignee: Energy and Environmental Research Center Foundation, Grand Forks, ND (US)

( * ) Notice: Subject to any disclaimer, the term of this patent is extended or adjusted under 35 U.S.C. 154(b) by 0 days.

(21) Appl. No.: 18/170,392

(22) Filed: Feb. 16, 2023

(65) Prior Publication Data

US 2023/0192499 A1 Jun. 22, 2023

Related U.S. Application Data

(63) Continuation-in-part of application No. 17/651,520, filed on Feb. 17, 2022, now Pat. No. 11,717,802.
(Continued)

(51) Int. Cl.
*C01B 32/50* (2017.01)
*B01J 23/80* (2006.01)
(Continued)

(52) U.S. Cl.
CPC .............. *C01B 32/50* (2017.08); *B01J 23/80* (2013.01); *C07C 29/154* (2013.01); *C25B 1/23* (2021.01);
(Continued)

(58) Field of Classification Search
None
See application file for complete search history.

(56) References Cited

U.S. PATENT DOCUMENTS 3,689,575 A * 9/1972 Tarhan ................. C07C 29/159
518/700
4,586,993 A 5/1986 Obrien
(Continued)

FOREIGN PATENT DOCUMENTS

AU 2012225322 A1 5/2013
EP 1899049 A2 3/2008
(Continued)

OTHER PUBLICATIONS

US 11,633,712 B2, 04/2023, Martin (withdrawn)
(Continued)

*Primary Examiner* — Chester T Barry
(74) *Attorney, Agent, or Firm* — Schwegman Lundberg & Woessner, P.A.

(57) ABSTRACT

A method of producing a syngas composition includes hydrolyzing a metal halide salt to form a hydrohalic acid and a hydroxide salt of the metal in the metal halide salt. The metal includes an alkaline earth metal or an alkali metal. The method includes reacting the hydrohalic acid with a metal carbonate salt, wherein the metal carbonate salt is a carbonate salt of the alkaline earth metal or alkali metal, to form $CO_2$ and the metal halide salt. At least some of the metal halide salt formed from the reacting of the hydrohalic acid with the metal carbonate salt is recycled as at least some of the metal halide salt in the hydrolyzing of the metal halide salt to form the hydrohalic acid and the hydroxide salt. The method also includes electrolytically converting the $CO_2$ and the water into the syngas composition including carbon monoxide and hydrogen.

20 Claims, 13 Drawing Sheets

Related U.S. Application Data

(60) Provisional application No. 63/200,390, filed on Mar. 4, 2021.

(51) Int. Cl.
    *C07C 29/154*    (2006.01)
    *C25B 13/07*     (2021.01)
    *C25B 15/08*     (2006.01)
    *C25B 9/19*      (2021.01)
    *C25B 1/23*      (2021.01)

(52) U.S. Cl.
    CPC ............... *C25B 9/19* (2021.01); *C25B 13/07* (2021.01); *C25B 15/081* (2021.01)

(56) References Cited

U.S. PATENT DOCUMENTS

| | | | |
|---|---|---|---|
| 4,704,265 | A | 11/1987 | Krohn et al. |
| 7,618,606 | B2 | 11/2009 | Fan et al. |
| 8,226,917 | B2 | 7/2012 | Fan et al. |
| 8,501,105 | B2 | 8/2013 | Fan et al. |
| 8,506,915 | B2 | 8/2013 | Abanades et al. |
| 8,540,954 | B2 | 9/2013 | Olsen |
| 8,795,508 | B2 | 8/2014 | Jones |
| 9,205,375 | B2 | 12/2015 | Jones et al. |
| 9,359,221 | B2 | 6/2016 | Jones et al. |
| 10,583,394 | B2 | 3/2020 | Jones et al. |
| 11,554,357 | B2 | 1/2023 | Martin |
| 11,717,802 | B2 | 8/2023 | Martin |
| 2006/0093540 | A1 | 5/2006 | Fan |
| 2008/0233029 | A1 | 9/2008 | Fan |
| 2009/0107850 | A1* | 4/2009 | Fang ................ C25B 13/08 205/521 |
| 2009/0127127 | A1 | 5/2009 | Jones |
| 2009/0214408 | A1 | 8/2009 | Blake et al. |
| 2010/0137457 | A1* | 6/2010 | Kaplan ............ C07C 29/1516 518/702 |
| 2011/0091366 | A1 | 4/2011 | Kendall et al. |
| 2012/0034144 | A1 | 2/2012 | Jones et al. |
| 2012/0128559 | A1 | 5/2012 | Olsen |
| 2013/0078159 | A1 | 3/2013 | Fan et al. |
| 2013/0202516 | A1 | 8/2013 | Jones et al. |
| 2013/0280152 | A1 | 10/2013 | Singh |
| 2014/0154162 | A1 | 6/2014 | Fan et al. |
| 2017/0292197 | A1* | 10/2017 | Lei ..................... C25B 9/19 |
| 2018/0043307 | A1 | 2/2018 | Jones et al. |
| 2019/0232216 | A1 | 8/2019 | Imbabi et al. |
| 2020/0316524 | A1 | 10/2020 | Jones et al. |
| 2022/0288556 | A1 | 9/2022 | Martin |
| 2022/0288557 | A1 | 9/2022 | Martin |
| 2023/0219057 | A1 | 7/2023 | Martin |

FOREIGN PATENT DOCUMENTS

| | | | |
|---|---|---|---|
| EP | 1948349 | A2 | 7/2008 |
| EP | 2118004 | A1 | 11/2009 |
| EP | 2200732 | A1 | 6/2010 |
| EP | 2207753 | A1 | 7/2010 |
| EP | 2240257 | A1 | 10/2010 |
| EP | 2291550 | A1 | 3/2011 |
| EP | 2384520 | A1 | 11/2011 |
| EP | 2305366 | B1 | 5/2012 |
| EP | 2512633 | A1 | 10/2012 |
| EP | 2590729 | A2 | 5/2013 |
| EP | 2236586 | B1 | 7/2014 |
| EP | 2808073 | A1 | 12/2014 |
| EP | 2809427 | A1 | 12/2014 |
| EP | 2724771 | B1 | 9/2015 |
| EP | 2464445 | B1 | 4/2017 |
| EP | 3261991 | A1 | 1/2018 |
| EP | 3484817 | A1 | 5/2019 |
| JP | H08947 | A | 1/1996 |
| KR | 20100079827 | A | 7/2010 |
| WO | WO-2009039445 | A3 | 12/2009 |
| WO | WO-2010137995 | A1 | 12/2010 |
| WO | WO-2012006601 | A3 | 8/2013 |
| WO | WO-2014205295 | A1 | 12/2014 |
| WO | WO-2016138016 | A1 | 9/2016 |
| WO | WO-2018011567 | A1 | 1/2018 |

OTHER PUBLICATIONS

"Carbonate Chemistry" article at https://www.sciencelearn.org.nz/resources/469-carbonate-chemistry downloaded Jun. 2, 2023 (Year: 2023).*
https://netl.doe.gov/research/coal/energy-systems/gasification/gasifipedia/water-gas-shift, downloaded Jun. 1, 2023 (Year: 2023).*
"Sodium Bicarbonate," https://en.wikipedia.org/wiki/Sodium_bicarbonate#:~: text=Sodium%20bicarbonate%20reacts%20with%20bases,CO3%20%2B%20H2O, downloaded Jun. 2, 2023 (Year: 2023).*
"U.S. Appl. No. 17/651,520 Preliminary Amendment".
"U.S. Appl. No. 17/651,520, Non Final Office Action dated Oct. 13, 2022", 9 pgs.
"U.S. Appl. No. 17/651,520, Notice of Allowance dated Dec. 14, 2022", 5 pgs.
"U.S. Appl. No. 17/651,520, Response filed Oct. 27, 2022 to Non Final Office Action dated Oct. 13, 2022", 9 pgs.
"U.S. Appl. No. 17/826,967, Final Office Action dated Oct. 13, 2022", 6 pgs.
"U.S. Appl. No. 17/826,967, Non Final Office Action dated Aug. 16, 2022", 13 pgs.
"U.S. Appl. No. 17/826,967, Notice of Allowance dated Nov. 2, 2022", 8 pgs.
"U.S. Appl. No. 17/826,967, Response filed Sep. 20, 2022 to Non Final Office Action dated Aug. 16, 2022", 12 pgs.
"U.S. Appl. No. 17/826,967, Response filed Oct. 18, 2022 to Final Office Action dated Oct. 13, 2022", 7 pgs.
"Direct Air Capture of CO2 with Chemicals", A Technology Assessment for the APS Panel on Public Affairs, (Jun. 1, 2011), 100 pgs.
"European Application Serial No. 22159507.7, Extended European Search Report dated Jul. 15, 2022", 8 pgs.
"European Application Serial No. 22159507.7, Response filed Sep. 7, 2022 to Extended European Search Report dated Jul. 15, 2022", 13 pgs.
"Innovation Outlook—Renewable Methanol", International Renewable Energy Agency (IRENA), Abu Dhabi, UAE, (2021), 124 pgs.
"Regeneration Solution for CO2 Direct Air Capture Solvents AOI-1 Development of Novel Materials for Direct Air Capture of CO2", Project Narrative, DE-FOA-0002188, Energy and Environmental Research Center, University of North Dakota, (May 28, 2020), 36 pgs.
Bischoff, James L, et al., "The generation of HCl in the system CaCl2-H2O: Vapor-liquid relations from 380-500° C.", Geochimica et Cosmochimica Acta, 60(1), Elsevier Science Ltd, USA, (1996), 7-16.
Eloy, Sanz-Perez S, et al., "Direct Capture of CO2 from Ambient Air", Chem. Rev., 2016, (2016), 11840-11876.
Ferguson, K. M., et al., "Production of Carbon Neutral Methanol Using Co-Electrolysis of CO2 and Steam in Solid Oxide Electrolysis Cell in Tandem with Direct Air Capture", ECS Transactions, 103 (1), (2021), 663-676.
Ghezel-Ayagh, Hossein, "Performance Improvements for Reversible Solid Oxide Fuel Cell Systems", FuelCell Energy, 2022 SOFC Project Review Meeting, Pittsburgh, PA, USA, (Oct. 26, 2022), 41 pgs.
Keith, David W, et al., "A Process for Capturing CO2 from the Atmosphere", Joule, 2(8), Elsevier, (2018), 1573-1594.
Klaus, Ziock, Lackner, et al., "Carbon Dioxide Extraction from Air: Is It an Option?", United States:1999. Web, (1999), 15 pgs.
Marina, O.A., et al., "Low Cost, Large Area SOEC Stack for H 2 and Chemicals", U.S. Department of Energy (FWP-77108), 23rd Annual Solid Oxide Fuel Cell (SOFC) Project Review Meeting, (Oct. 25, 2022), 22 pgs.

(56) References Cited

OTHER PUBLICATIONS

Martin, Christopher, "Hydrolytic Softening of ocean Water for Carbon Dioxide Removal", DE-FOA-0001953 Technical Volume, UND EERC, (Jul. 22, 2020), 21 pgs.

Musial, Walter, et al., "Survey and Assessment of the Ocean Renewable Resources in the US Gulf of Mexico", OCS Study BOEM 2020-017, U.S. Department of the Interior (DOI) Bureau of Ocean Energy Management (BOEM), New Orleans, LA, USA, (Feb. 2020), 82 pgs.

Probstein, Ronald F, et al., "Synthetic Fuels", Dover Publications, Inc., NY, USA, (1996), 463 pgs.

"White House Fact Sheet. Biden-Harris Administration Announces New Actions to Expand U.S. Offshore Wind Energy", [Online] Retrieved from the Internet: URL: www.whitehouse.gov briefing-room statements-releases Sep. 15, 2022 fact-sheet-biden-harris-administration-announces-new-actions-to-expand-u-s-offshore-wind-energy , (Sep. 14, 2022), 6 pgs.

"Launch of the Green Shipping Challenge at COP27", [Online] Retrieved from the Internet: URL: https: www.state.gov launch-of-the-green-shipping-challenge-at-cop27 , (Nov. 7, 2022), 6 pgs.

"Methanol Price Trend and Forecast", ChemAnalyst, [Online] Retrieved from the Internet: URL: https: web.archive.org web 20220930024909 https: www.chemanalyst.com Pricing-data methanol-1, (captured Sep. 30, 2022), 5 pgs.

"Sunfire-Synlink SOEC Product Sheet", Sunfire GmbH, (Nov. 2021), 2 pgs.

"New methanol plants expected to increase industrial natural gas use through 2020", U.S. Energy Information Administration, (Feb. 21, 2019), 3 pgs.

"Renewable Methanol Market", Allied Market Research, [Online] Retrieved from the Internet: URL: https: www.alliedmarketresearch.com renewable-methanol-market, (May 2020), 9 pgs.

Probstein, Ronald F, "Synthetic Fuels", Dover Publications, Inc., NY, USA, pp. 126-127, (2006), 3 pgs.

Turaga, Uday, "Small-Scale Methanol Technologies Offer Flexibility, Cost Effectiveness", Gas Processing and LNG, (Sep. 30, 2015), 11 pgs.

\* cited by examiner

US 11,858,819 B2

METHODS OF PRODUCING A SYNGAS COMPOSITION

CROSS-REFERENCE TO RELATED APPLICATIONS

This application is a continuation-in-part of and claims the benefit of priority under 35 U.S.C. § 120 to U.S. Utility application Ser. No. 17/651,520 filed Feb. 17, 2022, now U.S. Pat. No. 11,717,802, which claims the benefit under 35 U.S.C. § 119(e) to U.S. Provisional Patent Application Ser. No. 63/200,390 filed Mar. 4, 2021, the disclosures of which are incorporated herein in their entirety by reference.

BACKGROUND

Despite the high regeneration energy requirements for hydroxide-based solvents like KOH, $CO_2$ direct air capture (DAC) systems based on it are being actively commercialized primarily because of the implementation advantages of solvents over DAC alternatives such as solid sorbents and $CO_2$ selective membranes. These latter alternatives can have lower specific energy requirements compared to calcination-based regeneration, but only solvent capture currently appears advanced enough to successfully address the engineering challenges associated with large-scale air contactor design and function.

Solvent DAC systems are built around simple liquid-gas contactors for $CO_2$ absorption and centralized facilities for solvent regeneration. These systems can be robust since the active material (e.g., the liquid capture solvent), can be continually reconditioned while circulating, without having to pause $CO_2$ capture for a regeneration cycle. Basic liquid-air contactor models exist in the form of cost-effective cooling towers that are already implemented at the scales being discussed for global DAC impact. Also, by centrally regenerating the $CO_2$-rich solvent instead of distributing that function throughout the air contactor, it is possible for solvent regeneration to take advantage of equipment economies of scale, in contrast to sorbents and membranes which scale linearly through the addition of multiple units.

The active DAC component of sorbent-based systems, in contrast, is generally immobile, and provisions for capture, regeneration, and $CO_2$ desorption must be incorporated into the air contactor itself. Therefore, the advantage of a sorbent system's lower regeneration temperature compared to a solvent would seem to be offset by the need to cyclically distribute low-grade thermal energy throughout a large air-contacting structure.

Membrane-based DAC has a similar area-related drawback in that the active element, i.e., the membrane, serves as the air contactor interface, and a driving pressure gradient (with one side likely under vacuum) must be maintained across the entire surface. Given the small $CO_2$ pressure gradient that is available in the atmosphere, leaks anywhere throughout the system greatly degrade DAC performance.

The world's oceans are estimated to have absorbed roughly one-third of the $CO_2$ added to the atmosphere from human activities, lowering its pH by 0.1 units in the process. This accumulation affects the health of the oceans since $CO_2$ acidification contributes to coral bleaching and it hinders the growth of shell-forming marine animals. As such, large-scale ocean $CO_2$ removal using lime addition has been identified as a potential tool to improve the health of the oceans and to also possibly assist with moderating atmospheric $CO_2$ levels. However, the concept was based on the one-time consumption of lime to sequester ocean $CO_2$ as limestone, $CaCO_3$, which would require a significant lime production source.

In another approach to ocean $CO_2$ removal, NaCl is electrochemically split to form HCl and NaOH, and the HCl is used to lower the pH of seawater, thereby converting bicarbonate and driving off $CO_2$ gas. The NaOH is used to return pH to a normal range. Although bipolar membrane electrodialysis (EDBM) had advantages for producing HCl and NaOH from NaCl regarding feed water purification compared to chlor-alkali electrolysis and has a lower theoretical minimum energy requirement, in terms relative to $CO_2$ removal, the energy consumption of state of the art EDBM is unacceptably high; the minimum energy requirement is 2.3 kWe/kg to produce weakly concentrated NaOH. Based on this value of electricity consumption and assuming a 1:1 molar utilization of NaOH to $CO_2$ gas, the EDBM approach to $CO_2$ removal would require at least +331 kJ/mol $CO_2$ of energy input; at $60/MWhe, the energy cost alone would exceed $114/ton $CO_2$. Improvements with or alternatives to NaCl salt-splitting technology are needed to achieve cost targets below $100/ton $CO_2$.

Syngas, or synthesis gas, is a mixture of hydrogen and carbon monoxide. It can be used as a fuel, or used to produce various products including ammonia, methanol, liquid fuels, lubricants, gasoline, and/or oxo alcohols. Carbon-neutral syngas is made with $CO_2$ extracted from the environment so that, when the derivative fuels or chemicals are consumed, there is no net release of $CO_2$ back to the environment. Methods exist for producing carbon-neutral syngas, such as biomass gasification, but there is a need to develop scalable methods that directly convert carbon-neutral power sources into syngas to produce carbon-neutral fuels and chemicals.

SUMMARY OF THE INVENTION

A method of forming a syngas composition includes hydrolyzing a metal halide salt to form a hydrohalic acid and a hydroxide salt of the metal in the metal halide salt. The metal includes an alkaline earth metal or an alkali metal. The method includes reacting the hydrohalic acid with a metal carbonate salt, wherein the metal carbonate salt is a carbonate salt of the alkaline earth metal or alkali metal, to form $CO_2$, water, and the metal halide salt. At least some of the metal halide salt formed from the reacting of the hydrohalic acid with the metal carbonate salt is recycled as at least some of the metal halide salt in the hydrolyzing of the metal halide salt to form the hydrohalic acid and the hydroxide salt. The method also includes electrolytically converting the $CO_2$ and the water into the syngas composition including carbon monoxide and hydrogen A method of forming a syngas composition includes hydrolyzing $CaCl_2$) to form HCl and $Ca(OH)_2$. The method includes reacting the HCl with $CaCO_3$, to form $CO_2$, water, and $CaCl_2$), wherein at least some of the $CaCl_2$) formed from the reacting of the HCl with the $CaCO_3$ is recycled as at least some of the $CaCl_2$) in the hydrolyzing of the $CaCl_2$) to form the HCl and the $Ca(OH)_2$. The method also includes electrolytically converting the $CO_2$ and the water into the syngas composition including carbon monoxide and hydrogen.

A method of regenerating a used hydroxide-based $CO_2$-capture sorbent includes hydrolyzing a metal halide salt to form a hydrohalic acid and a hydroxide salt of the metal in the metal halide salt. The metal includes an alkaline earth metal or an alkali metal. The method includes reacting the used hydroxide-based $CO_2$-capture sorbent with the hydroxide salt, to form a carbonate salt of the metal in the metal halide salt. The method includes reacting the hydrohalic acid with the carbonate salt, to form $CO_2$, water, and the metal halide salt. At least some of the metal halide salt formed from the reacting of the hydrohalic acid with the carbonate salt is recycled as at least some of the metal halide salt in the hydrolyzing of the metal halide salt to form the hydrohalic acid and the hydroxide salt. The method also includes electrolytically converting the $CO_2$ and the water into a syngas composition including carbon monoxide and hydrogen.

A method of regenerating a used hydroxide-based $CO_2$-capture sorbent includes hydrolyzing $CaCl_2$ to form HCl and $Ca(OH)_2$. The method includes reacting the used hydroxide-based $CO_2$-capture sorbent with the $Ca(OH)_2$, to form $CaCO_3$. The method includes reacting the HCl with the $CaCO_3$, to form $CO_2$, water, and $CaCl_2$. At least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$. The method also includes electrolytically converting the $CO_2$ and the water into a syngas composition including carbon monoxide and hydrogen.

A method of producing a syngas composition includes hydrolyzing a metal halide salt to form a hydrohalic acid and a hydroxide salt of the metal in the metal halide salt, the metal including an alkaline earth metal or an alkali metal. The method includes reacting a bicarbonate salt from a water source including ocean water with the hydroxide salt, to form a carbonate salt of the metal in the metal halide salt. The method includes reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt. The method also includes electrolytically converting the $CO_2$ and the water into the syngas composition including carbon monoxide and hydrogen.

A method of producing methanol includes hydrolyzing a metal halide salt to form a hydrohalic acid and a hydroxide salt of the metal in the metal halide salt, the metal including an alkaline earth metal or an alkali metal. The method includes reacting a bicarbonate salt from a water source including ocean water with the hydroxide salt, to form a carbonate salt of the metal in the metal halide salt. The method includes reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt. The method includes electrolytically converting the $CO_2$ and the water into a syngas composition including carbon monoxide and hydrogen. The method also includes reacting the carbon monoxide and the hydrogen in the presence of a catalyst to form the methanol.

A method of producing a syngas composition includes hydrolyzing $CaCl_2$ to form HCl and $Ca(OH)_2$. The method includes reacting $Ca(HCO_3)_2$ from a water source including ocean water with the $Ca(OH)_2$, to form $CaCO_3$. The method includes reacting the HCl with the $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$. The method also includes electrolytically converting the $CO_2$ and the water into the syngas composition including carbon monoxide and hydrogen.

A method of producing methanol includes hydrolyzing $CaCl_2$ to form HCl and $Ca(OH)_2$. The method includes reacting $Ca(HCO_3)_2$ from a water source including ocean water with the $Ca(OH)_2$, to form $CaCO_3$. The method includes reacting the HCl with the $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$. The method includes electrolytically converting the $CO_2$ and the water into a syngas composition including carbon monoxide and hydrogen. The method includes reacting the carbon monoxide and the hydrogen in the presence of a catalyst to form the methanol.

Various aspects of the methods of the present invention have advantages over other methods. For example, various aspects of the method of producing a syngas composition can be used as an alternative to the calcination of limestone for the production of hydrated lime. The formed hydrohalic acid can be used to decompose natural limestone, resulting in a metal halide salt solution that can be hydrolyzed to form hydrated lime. An advantage of this process compared to conventional limestone calcination is the use of less energy; brine hydrolysis could lower the heat source temperature from 900° C. to 400° C. or lower. Also, by incorporating the exothermic lime hydration reaction into the hydrolysis step (i.e., CaO to $Ca(OH)_2$), the minimum required thermal energy can be lowered by 28%, from 178 kJ/mol $CaCO_3$ for calcination to 128 kJ/mol $CaCO_3$ for the present invention. Additionally, the $CO_2$ released from limestone decomposition can be isolated (e.g., from flue gases) and readily captured for sequestration. The cement production industry can benefit from aspects of the method of producing a syngas composition, as this energy-intensive industry struggles to efficiently decarbonize.

Hydroxide-based $CO_2$-capture sorbents such as KOH and NaOH have desirable properties when it comes to DAC; e.g., they can be used in large, scalable air contactors and can capture $CO_2$ continuously without pausing air flow for regeneration. However, a feature that makes these solvents attractive for DAC, their high affinity for $CO_2$, also makes them costly to regenerate, various aspects of the present invention address that deficiency. In particular, existing solvent regeneration schemes using Ca causticization use the direct calcination (thermal decomposition) of $CaCO_3$ to release the $CO_2$ product and regenerate the CaO capture material. This process occurs at high temperatures (900° C. or greater) and has a significant endothermic heat of reaction of approximately 178 kJ/mol $CO_2$. Various aspects of the present method that use hydrolyzed $CaCl_2$) salt as a reaction intermediary can lower the required temperature to below 500° C., which can expand the types of heat resources suitable for regeneration. In various aspects, by incorporating $Ca(OH)_2$ formation into the overall reaction, the theoretical input energy requirements can be decreased, such as brought down to approximately 113 kJ/mol $CO_2$, since the hydroxide formation is exothermic. Conventional calcination produces CaO solids that must be separately slaked with water to produce $Ca(OH)_2$. Low grade heat is released by lime slaking and can be recovered for drying, etc., but this energy cannot be used to offset the calciner's high temperature energy demands.

In various aspects, the method of regenerating a used $CO_2$-sorbent can require a lower amount of energy than other methods of regenerating used $CO_2$-sorbents, making direct air capture for removal of $CO_2$ a more viable carbon management tool. In various aspects, the method of regenerating a used $CO_2$-sorbent can expand the feasible use of hydroxide solvents such as KOH by reducing the temperature and quantity of regeneration energy. Hydroxide solvents have strong chemisorption capacity for $CO_2$, making them effective even with the low $CO_2$ partial pressure in the atmosphere, and have been the preferred choice for $CO_2$ DAC studies and pilot tests over amines that are considered the benchmark for postcombustion $CO_2$ capture. Regeneration energy has been the primary drawback of hydroxide solvents, and the lower-temperature, lower-energy regeneration methods of the present invention can make them a superior choice for DAC compared to materials that operate at higher $CO_2$ concentrations.

In various aspects, the method of the present invention of removing $CO_2$ from water can recycle the metal and halide constituents, as contrasted with an electrochemical NaCl-based process where the split NaOH and HCl constituents are released with the treated seawater and replacement NaCl brine must be reconcentrated. In various aspects, the brine hydrolysis of the present invention can be more robust (e.g., can be more tolerant of other dissolved species found in seawater) and lower cost to operate. Excessive energy consumption hinders ocean $CO_2$ removal by increasing operating costs and creating additional $CO_2$ emissions that need to be offset. The method of the present invention of removing $CO_2$ from water can provide a thermochemical cycle to achieve production of $CO_2$ from bicarbonate while enabling a lower cost of energy consumption compared to what is possible today, making the concept of ocean $CO_2$ removal a more feasible tool for carbon management. Compared to a NaCl-based process, the hydrolytic softening method described herein can be less disruptive to ocean life since it does not acidify the water which could harm sensitive organisms. As a result, the hydrolytic softening of the present invention can present a relatively lower environmental risk and should face fewer restrictions on its application.

In various aspects, methods of the present invention can use commodity materials, which can be an advantage over other methods that require proprietary, tailored materials that may introduce bottlenecks to future large-scale deployment.

In various aspects, the water and the carbon dioxide formed by the reaction of the hydrohalic acid with the metal carbonate salt are in a gaseous state, which advantageously provides for efficient electrolysis of the water and carbon dioxide to the syngas composition. In various aspects, the syngas composition is converted to other materials such as methanol, and heat released via exothermic reaction to form the other materials can be recycled back into the method, providing enhanced efficiency.

In various aspects, the method includes forming the syngas composition using ocean water can also include forming methanol from the syngas composition, which can result in carbon-neutral syngas and methanol since the feedstock carbon dioxide is harvested directly from the ocean-atmosphere interface instead of being derived from a fossil resource. Compared to biomass-based approaches for producing carbon-neutral syngas or methanol, such embodiments of the present invention avoid land-based resource competitions, including access to arable land and water and competition with food production. If operated offshore, such embodiments of the present invention can also leverage existing offshore petroleum infrastructure by situating facilities at end-of-life oil and gas platforms and using by existing transport pipelines to transport the syngas or methanol to shore.

In various aspects, the method of the present invention produces a carbon-neutral syngas, made with $CO_2$ extracted from the environment, such that when derivative fuels or chemicals are consumed, there is no net release of $CO_2$ back to the environment. Unlike land-based biomass gasification, various embodiments the present method can be more easily scaled, such as to more conveniently produce larger quantities of carbon-neutral syngas or materials therefrom.

BRIEF DESCRIPTION OF THE FIGURES

The drawings illustrate generally, by way of example, but not by way of limitation, various aspects of the present invention.

DETAILED DESCRIPTION OF THE INVENTION

Figure 1:
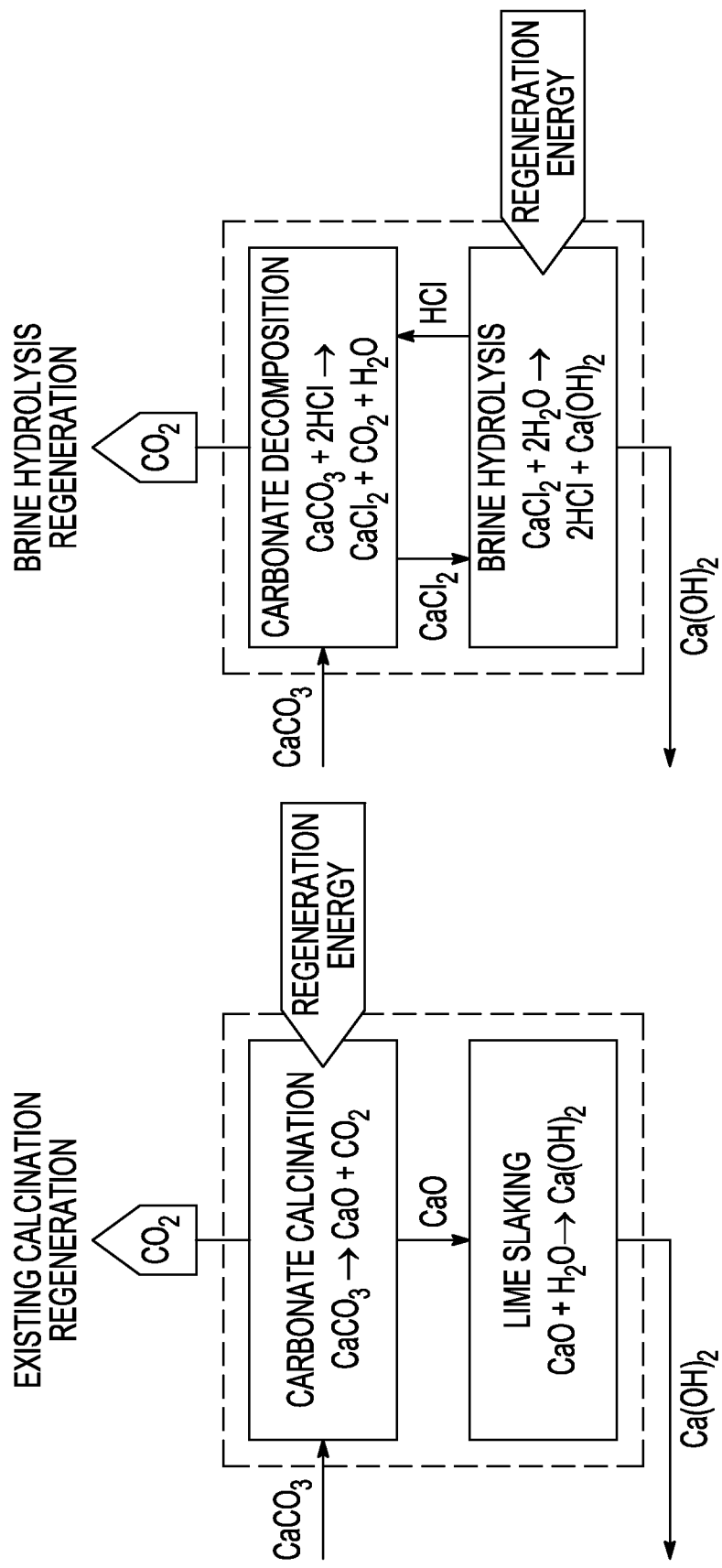
FIG. 1 illustrates a process comparison between calcination and brine hydrolysis regeneration, in accordance with various aspects.

Reference will now be made in detail to certain aspects of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Method of Producing a Syngas Composition.

Various aspects of the present invention provide a method of producing a syngas composition. The method can include hydrolyzing a metal halide salt to form a hydrohalic acid and a hydroxide salt of the metal in the metal halide salt. The metal can include an alkaline earth metal or an alkali metal. The method can include reacting the hydrohalic acid with the metal carbonate salt, wherein the metal carbonate salt is a carbonate salt of the alkaline earth metal or alkali metal, to form $CO_2$, water, and the metal halide salt. At least some of the metal halide salt formed from the reacting of the hydrohalic acid with the metal carbonate salt can be recycled as at least some of the metal halide salt in the hydrolyzing of the metal halide salt to form the hydrohalic acid and the hydroxide salt. The method can also include electrolytically converting the $CO_2$ and the water into the syngas composition including carbon monoxide and hydrogen.

The metal carbonate salt can be any suitable metal carbonate salt. In some examples, the metal carbonate salt is $BeCO_3$, $MgCO_3$, $CaCO_3$, $SrCO_3$, $BaCO_3$, $RaCO_3$, $Li_2CO_3$, $Na_2CO_3$, $K_2CO_3$, $Rb_2CO_3$, $Cs_2CO_3$, $Fr_2CO_3$, or a combination thereof. The metal carbonate salt can be $CaCO_3$, $MgCO_3$, or a combination thereof. The metal carbonate salt can be $CaCO_3$.

The metal carbonate salt can be from any suitable source, such as from a sorbent, a water source (e.g., salt water, fresh water, or ocean water), or a combination thereof. The metal carbonate salt can be $CaCO_3$ and the $CaCO_3$ can be produced from a $CO_2$-capture sorbent, is a $CaCO_3$ precipitate formed from water softening, is natural limestone (e.g., as used in the cement industry, or another industry), or a combination thereof.

The method can include hydrolyzing a metal halide salt to form a hydrohalic acid and a hydroxide salt of the metal in the metal halide salt. The metal can include an alkaline earth metal or an alkali metal, such as beryllium, magnesium, calcium, strontium, barium, radium, lithium, sodium, potassium, rubidium, cesium, francium, or a combination thereof. The alkaline earth metal or alkali metal can be magnesium, calcium, or a combination thereof. The alkaline earth metal or alkali metal can be calcium.

The metal halide salt can be beryllium halide salt, a magnesium halide salt, a calcium halide salt, a strontium halide salt, a barium halide salt, a radium halide salt, a lithium halide salt, a sodium halide salt, a potassium halide salt, a rubidium halide salt, a cesium halide salt, a francium halide salt, or a combination thereof. The halide can be chloride and the metal halide salt can be beryllium chloride, magnesium chloride, calcium chloride, strontium chloride, barium chloride, radium chloride, lithium chloride, sodium chloride, potassium chloride, rubidium chloride, cesium chloride, francium chloride, or a combination thereof. The metal halide salt can be $CaCl_2$, $MgCl_2$, or a combination thereof. The metal halide salt can be $CaCl_2$. The hydrohalic acid can be HCl, HBr, HI, HF, or a combination thereof. The hydrohalic acid can be HCl. The hydroxide salt can be $Be(OH)_2$, $Mg(OH)_2$, $Ca(OH)_2$, $Sr(OH)_2$, $Ba(OH)_2$, $Ra(OH)_2$, LiOH, NaOH, KOH, RbOH, CsOH, FrOH, or a combination thereof. The hydroxide salt can be $Ca(OH)_2$, $Mg(OH)_2$, or a combination thereof. The hydroxide salt can be $Ca(OH)_2$.

In some aspects, the metal carbonate salt is $CaCO_3$, the alkaline earth metal or alkali metal is calcium, the metal halide salt is $CaCl_2$, the hydrohalic acid is HCl, and the hydroxide salt is $Ca(OH)_2$.

The hydrolyzing of the metal halide salt can be performed under any suitable conditions. The hydrolyzing of the metal halide salt can be performed at any suitable pressure, such as at a pressure of 0.1 MPa-100 Mpa, or 0.1 Mpa to 9 Mpa, or 1 Mpa to 9 Mpa, or 3 Mpa to 9 Mpa, or 5 Mpa to 7 Mpa, or less than, equal to, or greater than 0.1 Mpa, 0.5, 1, 2, 3, 4, 5, 6, 7, 8, 9, 10, 12, 14, 16, 18, 20, 25, 30, 40, 50, 60, 70, 80, 90, or 100 Mpa. The hydrolyzing of the metal halide salt can be performed at any suitable temperature, such as a temperature of room temperature to 1000° C., or room temperature to 500° C., or 300° C. to 500° C., or 350° C. to 450° C., or less than, equal to, or greater than room temperature (e.g., about 20° C.), 25, 30, 35, 40, 45, 50, 60, 80, 100, 125, 150, 175, 200, 225, 250, 275, 300, 320, 340, 350, 360, 370, 380, 390, 400, 410, 420, 430, 440, 450, 460, 480, 500, 550, 600, 650, 700, 750, 800, 850, 900, 950, or 1000° C.

The hydrolyzing of the metal halide salt (i.e., in water) produces the hydrohalic acid. The hydrohalic acid can be produced in a phase that is distinct from the brine solution that includes the water and the metal halide salt. The acid/water phase can be a vaporous phase, a supercritical water phase, a gaseous phase, or a combination thereof, depending on the hydrolysis conditions used to form the hydrohalic acid. The hydrolyzing of the metal halide salt can produce the hydrohalic acid at any suitable concentration (e.g., in the distinct acid/water phase), such as at a molar content of 0.01% to 10%, or a molar content of 0.1% to 1%, or less than, equal to, or greater than 0.01%, 0.05, 0.1, 0.2, 0.3, 0.4, 0.5, 0.6, 0.7, 0.8, 0.9, 1, 1.1, 1.2, 1.3, 1.4, 1.5, 1.8, 2, 2.5, 3, 3.5, 4, 4.5, 5, 5.5, 6, 6.5, 7, 7.5, 8, 8.5, 9, 9.5, or 10% molar content.

The reacting of the hydrohalic acid with the metal carbonate salt can be performed under any suitable conditions. The reacting of the hydrohalic acid with the metal carbonate salt can be performed in the same reactor with, and using the same conditions as, the hydrolysis of the metal halide salt to form the hydrohalic acid (e.g., a heated and pressurized reactor). The reacting of the hydrohalic acid with the metal carbonate salt can be performed in a separate reactor from the reacting of the hydrolysis of the metal halide salt to form the hydrohalic acid, such as by removing the hydrohalic acid from the reactor, cooling the hydrohalic acid, and performing the reacting of the hydrohalic acid with the metal carbonate salt under different conditions, such as room temperature/pressure conditions. The reacting of the hydrohalic acid with the metal carbonate salt can be performed at a pressure of 0.1 Mpa-100 Mpa, or 0.1 Mpa to 9 Mpa, or 1 Mpa to 9 Mpa, or 3 Mpa to 9 Mpa, or 5 Mpa to 7 Mpa, or less than, equal to, or greater than 0.1 Mpa, 0.5, 1, 2, 3, 4, 5, 6, 7, 8, 9, 10, 12, 14, 16, 18, 20, 25, 30, 40, 50, 60, 70, 80, 90, or 100 Mpa. The reacting of the hydrohalic acid with the metal carbonate salt can be performed at a temperature of room temperature to 1000° C., or room temperature to 500° C., or 300° C. to 500° C., or 350° C. to 450° C., or less than, equal to, or greater than room temperature (e.g., about 20° C.), 25, 30, 35, 40, 45, 50, 60, 80, 100, 125, 150, 175, 200, 225, 250, 275, 300, 320, 340, 350, 360, 370, 380, 390, 400, 410, 420, 430, 440, 450, 460, 480, 500, 550, 600, 650, 700, 750, 800, 850, 900, 950, or 1000° C.

At least some of the metal halide salt formed from the reacting of the hydrohalic acid with the metal carbonate salt can be recycled as at least some of the metal halide salt in the hydrolyzing of the metal halide salt to form the hydrohalic acid and the hydroxide salt. The metal halide salt formed from the reacting of the hydrohalic acid with the metal carbonate salt can be any suitable proportion of the metal halide salt used in the hydrolyzing of the metal halide salt to form the hydrohalic acid and the hydroxide salt. For example, the metal halide salt formed from the reacting of the hydrohalic acid with the metal carbonate salt is 0.001 wt % to 100 wt % of the metal halide salt used in the hydrolyzing of the metal halide salt to form the hydrohalic acid and the hydroxide salt, or 80 wt % to 100 wt %, or less than, equal to, or greater than 0.001 wt %, 0.01, 0.1, 1, 2, 3, 4, 5, 6, 8, 10, 15, 20, 25, 30, 35, 40, 45, 50, 55, 60, 65, 70, 75, 80, 85, 90, 91, 92, 93, 94, 95, 96, 97, 98, 99, 99.9, 99.99, or 99.999 wt %, or 100 wt %.

Various aspects provide a method of treating $CaCO_3$ to form a syngas composition. The method can include hydrolyzing $CaCl_2$ to form HCl and $Ca(OH)_2$. The method can include reacting the HCl with the $CaCO_3$, to form $CO_2$, water, and $CaCl_2$, wherein at least some of the $CaCl_2$) formed from the reacting of the HCl with the $CaCO_3$ is recycled as at least some of the $CaCl_2$) in the hydrolyzing of the $CaCl_2$) to form the HCl and the $Ca(OH)_2$. The method can further include reacting a used $CO_2$-capture sorbent with the $Ca(OH)_2$, to form the $CaCO_3$, wherein at least some of the $Ca(OH)_2$ formed in the hydrolysis of the $CaCl_2$) to form the HCl and the $Ca(OH)_2$ is recycled as at least some of the $Ca(OH)_2$ used in the reacting of the used $CO_2$-capture sorbent with the $Ca(OH)_2$. The method can include reacting $Ca(HCO_3)_2$ from a water source with the $Ca(OH)_2$, to form the $CaCO_3$, wherein at least some of the $Ca(OH)_2$ formed in the hydrolysis of the $CaCl_2$) to form the HCl and the $Ca(OH)_2$ is recycled as at least some of the $Ca(OH)_2$ used in the reacting of the $Ca(HCO_3)_2$ with the $Ca(OH)_2$. The method can also include electrolytically converting the $CO_2$ and the water into a syngas composition including carbon monoxide and hydrogen The method of producing a syngas composition can be used to regenerate hydrated lime ($Ca(OH)_2$), such as from the precipitates produced during lime softening of water. Lime softening is a common treatment for municipal and industrial water supplies.

The method of producing a syngas composition can be used to produce hydrated lime or dolomitic lime (e.g., a mixture of $Ca(OH)_2$ and $Mg(OH)_2$). This process is already performed at large scale using calcination to produce lime for cement, steelmaking, food processing, and many other industries. The method of producing a syngas composition can be used to process a source of $CaCO_3$ to convert it into a $Ca(OH)_2$ product.

The method of producing a syngas composition can include reacting the hydrohalic acid with the metal carbonate salt, wherein the metal carbonate salt is a carbonate salt of the alkaline earth metal or alkali metal, to form $CO_2$, water, and the metal halide salt. The method of producing a syngas composition can include electrolytically converting the $CO_2$ and the water produced by the reacting of the hydrohalic acid with the metal carbonate salt into the syngas composition including carbon monoxide and hydrogen. The water formed by the reacting of the hydrohalic acid with the metal carbonate salt can be or can include gaseous water. The water formed during the reacting of the hydrohalic acid can have a temperature of 100° C. to 500° C., or 100° C. to 150° C., or less than or equal to 500° C. and greater than or equal to 100° C., 110, 120, 130, 140, 150, 160, 180, 200, 250, 300, 350, 400, or 450° C. Any suitable proportion of the water formed by the reacting the hydrohalic acid with the metal carbonate salt can be gaseous water; for example, 50-100 wt % of the water formed during the reacting of the hydrohalic acid can be gaseous water, or 90-100 wt %, or less than or equal to 100 wt % and greater than or equal to 50, 55, 60, 65, 70, 75, 80, 85, or 95 wt %.

The electrolytic conversion of the $CO_2$ can convert any suitable proportion of the $CO_2$ and the water to other products (such as carbon monoxide). For example, the electrolytic conversion of the $CO_2$ and the water into the syngas composition can convert 50% to 100% of the $CO_2$, or 90% to 100% of the $CO_2$, or less than or equal to 100 wt % and greater than or equal to 50, 55, 60, 65, 70, 75, 80, 85, or 95 wt % of the $CO_2$. For example, the electrolytic conversion of the $CO_2$ and the water into the syngas composition can convert 50% to 100% of the water, or 90% to 100% of the water, or less than or equal to 100 wt % and greater than or equal to 50, 55, 60, 65, 70, 75, 80, 85, or 95 wt % of the water.

The syngas composition includes carbon monoxide and hydrogen. Carbon monoxide can form any suitable proportion of the syngas composition, such as 15 mol % to 40 mol % of the syngas composition, or 30 mol % to 36 mol % of the syngas composition, or less than or equal to 40 mol % and greater than or equal to 15, 16, 17, 18, 19, 20, 21, 22, 23, 24, 25, 26, 27, 28, 29, 30, 31, 32, 33, 34, 35, 36, 37, 38, or 39 mol %. Hydrogen can form any suitable proportion of the syngas composition, such as 30 mol % to 80 mol % of the syngas composition, or 60 mol % to 75 mol % of the syngas composition, or less than or equal to 80 mol % and greater than or equal to 30 mol %, 35, 40, 45, 50, 55, 56, 57, 58, 59, 60, 61, 62, 63, 64, 65, 66, 67, 68, 69, 70, 71, 72, 73, 74, 75, 76, 77, 78, or 79 mol %. The syngas composition can have any suitable molar ratio of hydrogen to carbon monoxide, such as 1:1 to 3.5:1, 1.9:1 to 2.1:1, or less than or equal to 3.5:1 and greater than or equal to 1:1, 1.2:1, 1.4:1, 1.6:1, 1.8:1, 1.9:1, 2.0:1, 2.1:1, 2.2:1, 2.3:1, 2.4:1, 2.6:1, 2.8:1, 2.9:1, 3:1, 3.1:1, 3.2:1, or 3.4:1. Any suitable proportion of the syngas composition can be $CO_2$, such as 0 mol % to 20 mol %, or 0 mol % to 5 mol %, or less than or equal to 20 mol % or greater than or equal to 0 mol %, 1, 2, 3, 4, 5, 6, 8, 10, 12, 14, 16, or 18 mol %. Any suitable proportion of the syngas composition can be water, such as 0 mol % to 33 mol %, or 0 mol % to 10 mol %, or less than or equal to 33 mol % and greater than or equal to 0 mol %, 1, 2, 3, 4, 5, 6, 7, 8, 9, 10, 12, 14, 16, 18, 20, 22, 24, 26, 28, 30, or 32 mol %. In various embodiments, the method can include supplementing the water from the reaction of the hydrohalic acid with the metal carbonate salt (e.g., HCl with $CaCO_3$) with additional water to accomplish a desired molar ratio of hydrogen to carbon monoxide, such as by vaporizing a portion of the water entrained with the $CaCO_3$.

Electrolytically converting the $CO_2$ and the water into the syngas composition can include placing the $CO_2$ and/or the water into contact with an electrolytic cell. The electrolytic cell can be any suitable electrolytic cell that can convert the $CO_2$, the water, or both, to carbon monoxide and hydrogen. The electrolytic cell can include a reverse fuel cell, a solid oxide electrolysis cell, and/or a molten carbonate electrolysis cell. The electrolytic cell can include a solid oxide electrolysis cell. The electrolytic cell can include an anode, cathode, and an electrolyte, wherein at least one of the anode, cathode, and the electrolyte includes yttria-stabilized zirconia (YSZ). The electrolytic cell can include a cathode including Ni. The electrolytic cell can include an anode including lithium strontium manganite (LSM). The electrolytic cell can include an electrolyte including yttria-stabilized zirconia (YSZ), a cathode including Ni-YSZ, and an anode including lithium strontium manganite (LSM)-YSZ cathode.

The electrolytic cell can be a solid oxide electrolysis cell (SOEC) with yttria-stabilized zirconia (YSZ) electrolyte, Ni-YSZ cathode, and LSM-YSZ anode where LSM is Lanthanum Strontium Manganite. Such electrode assemblies can sandwich a YSZ electrolyte layer between the anode and cathode layers; this electrode structure can be formed into plates or tubes that can be used to create separate flow chambers for the CO, $H_2$, $CO_2$, and $H_2O$ gas mixture, and the 02 that is electrochemically separated.

Electrolytically converting the $CO_2$ and the water into the syngas composition can include placing the $CO_2$ into contact with a first electrolytic cell that electrolytically converts the $CO_2$ to CO, and placing the water into contact with a second electrolytic cell that electrolytically converts the $H_2O$ to $H_2$. Electrolytically converting the $CO_2$ and the water into the syngas composition can include placing the $CO_2$ and the water into contact with an electrolytic cell that electrolytically converts the $CO_2$ to CO and that electrolytically converts the $H_2O$ to $H_2$ (i.e., coelectrolysis). Electrolytically converting the $CO_2$ and the water into the syngas composition can include using (e.g., maintaining) the one or more electrolytic cells at a temperature of 500° C. to 1,000° C., or 700° C. to 800° C., or less than or equal to 1,000° C. and greater than or equal to 500° C., 550, 600, 650, 700, 720, 740, 760, 780, 800, 850, 900, or 950° C.

The method of producing the syngas composition can include using the syngas composition as a starting material to form a product including ammonia, methanol, a liquid fuel, a lubricant, gasoline, an oxo alcohol, or a combination thereof. The method can include using the syngas composition as a starting material in a Fischer-Tropsch process to form one or more hydrocarbons. The method can be a method of making methanol, wherein the method further includes using the syngas composition as a starting material to form methanol.

Forming the methanol can include reacting the CO and the hydrogen in the presence of a catalyst to form the methanol. The catalyst can be any suitable catalyst. For example, the catalyst can include Cr—Zn, Cu—Zr, and/or Cu—Zn. The catalyst can include a Cu—Zn catalyst. Forming the methanol can include reacting the CO and the hydrogen in the presence of the catalyst at any suitable temperature, such as a temperature of 20° C. to 500° C., or 200° C. to 300° C., or less than or equal to 500° C. and greater than or equal to 20° C., 40, 60, 80, 100, 120, 140, 160, 180, 200, 210, 220, 230, 240, 250, 260, 270, 280, 290, 300, 320, 340, 360, 380, 400, 450° C. Forming the methanol can include reacting the CO and the hydrogen in the presence of the catalyst at any suitable pressure, such as a pressure of 0.1 MPa to 40 MPa, 3 MPa to 10 MPa, or less than or equal to 40 MPa and greater than or equal to 0.1 MPa, 1, 2, 3, 4, 5, 6, 7, 8, 9, 10, 11, 12, 13, 14, 15, 16, 18, 20, 24, 26, 28, 30, 32, 34, 36, or 38 MPa.

The method can include recycling at least some exothermic heat generated by the formation of the product from the starting material in the method. Recycling at least some exothermic heat generated by the formation of the product from the starting material in the method can include supplying at least part of the generated exothermic heat to the reaction of the hydrohalic acid with the metal carbonate salt to form the metal halide salt.

Method of Regenerating a $CO_2$-Capture Sorbent.

The method of producing the syngas composition can be used to remove $CO_2$ from a used $CO_2$-capture sorbent (e.g., a $CO_2$-capture sorbent for air). The method can include reacting a used $CO_2$-capture sorbent with the hydroxide salt to provide the metal carbonate salt that is a carbonate salt of the metal in the metal halide salt. The used $CO_2$-capture sorbent can be any suitable used $CO_2$-capture sorbent, such as formed from contacting $CO_2$ with any suitable $CO_2$-capture sorbent. The used $CO_2$-capture sorbent can be a used hydroxide-based, ammonia-based, and/or amine-based $CO_2$-capture sorbent. In some examples, the used ammonia-based and/or amine-based $CO_2$-capture sorbent can include an ammonium carbamate, an ammonium carbonate, an ammonium bicarbonate, or a combination thereof. The used $CO_2$-capture sorbent can be derived from sorption of $CO_2$ by a hydroxide-based, ammonia-based (e.g., aqueous ammonia and/or ammonium bicarbonate), and/or amine-based $CO_2$-capture sorbent (e.g., monoethanolamine, diethanolamine, 2-amino-2-methyl-1-propanol, methyldiethanolamine, piperazine). The $CO_2$-capture sorbent can be a used hydroxide-based $CO_2$-capture sorbent, such as $Ca(HCO_3)_2$ (derived from $Ca(OH)_2$), $Mg(HCO_3)_2$ (derived from $Mg(OH)_2$), $K_2CO_3$ (derived from KOH), $Na_2CO_3$ (derived from NaOH), or a combination thereof.

The reacting of the used $CO_2$-capture sorbent with the hydroxide salt to provide the metal carbonate salt can be performed under any suitable conditions. The reacting of the used $CO_2$-capture sorbent with the hydroxide salt to provide the metal carbonate salt can be performed at a pressure of 0.01 MPa to 10 MPa, 0.05 MPa to 0.2 MPa, or less than, equal to, or greater than 0.01 MPa, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.4, 0.5, 0.6, 0.8, 1, 1.5, 2, 2.5, 3, 3.5, 4, 4.5, 5, 6, 7, 8, 9, or 10 MPa. The reacting of the used $CO_2$-capture sorbent with the hydroxide salt to provide the metal carbonate salt is performed at a temperature of room temperature to 350° C., or 50° C. to 150° C., or 90° C. to 110° C., or less than, equal to, or greater than room temperature 25, 30, 35, 40, 45, 50, 60, 70, 80, 85, 90, 95, 100, 105, 110, 115, 120, 120, 125, 150, 175, 200, 225, 250, 275, 300, 320, 340, or 350° C.

The method can include contacting a $CO_2$-capture sorbent with $CO_2$ to form the used $CO_2$-capture sorbent. In other aspects, the $CO_2$-capture sorbent is contacted with $CO_2$ to form the used $CO_2$-capture sorbent prior to the onset of the method. The method can include contacting $Ca(OH)_2$, $Mg(OH)_2$, KOH, and/or NaOH with $CO_2$ to form the used $CO_2$-capture sorbent.

The reacting of the used $CO_2$-capture sorbent with the hydroxide salt to form the metal carbonate salt can also form an unused $CO_2$-capture sorbent, e.g., to regenerate the used $CO_2$-capture sorbent. The unused $CO_2$-capture sorbent can be $Ca(OH)_2$, $Mg(OH)_2$, KOH, and/or NaOH. The unused $CO_2$-capture sorbent can be KOH and/or NaOH. The method can further include providing the unused $CO_2$-capture sorbent for $CO_2$ capture. The method can further include contacting the regenerated $CO_2$-capture sorbent with $CO_2$ to form a used $CO_2$-capture sorbent, which can then again be regenerated using the method.

In some aspects, none of the hydroxide salt formed in the hydrolysis of the metal halide salt to form the hydrohalic acid and the hydroxide salt is recycled as the hydroxide salt used in the reacting of the used $CO_2$-capture sorbent with the hydroxide salt. In other aspects, at least some of the hydroxide salt of the metal formed in the hydrolysis of the metal halide salt to form the hydrohalic acid and the hydroxide salt can be recycled as at least some of the hydroxide salt used in the reacting of the used $CO_2$-capture sorbent with the hydroxide salt. For example, the hydroxide salt of the metal formed in the hydrolysis of the metal halide salt can be 0.001 wt % to 100 wt % of the hydroxide salt used in the reacting of the used $CO_2$-capture sorbent with the hydroxide salt, or 80 wt % to 100 wt %, or less than, equal to, or greater than 0.001 wt %, 0.01, 0.1, 1, 2, 3, 4, 5, 6, 8, 10, 15, 20, 25, 30, 35, 40, 45, 50, 55, 60, 65, 70, 75, 80, 85, 90, 91, 92, 93, 94, 95, 96, 97, 98, 99, 99.9, 99.99, or 99.999 wt %, or 100 wt %.

The method of regenerating a used $CO_2$-capture sorbent can include hydrolyzing a metal halide salt to form a hydrohalic acid and a hydroxide salt of the metal in the metal halide salt, the metal including an alkaline earth metal or an alkali metal. The method can include reacting the used $CO_2$-capture sorbent with the hydroxide salt, to form a carbonate salt of the metal in the metal halide salt. The method can also include reacting the hydrohalic acid with the carbonate salt, to form $CO_2$ and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt.

The method of forming a syngas composition can include hydrolyzing $CaCl_2$ to form HCl and $Ca(OH)_2$. The method can include reacting the used $CO_2$-capture sorbent with the $Ca(OH)_2$, to form $CaCO_3$. The method can also include reacting the HCl with the $CaCO_3$, to form $CO_2$, water, and $CaCl_2$), wherein at least some of the $CaCl_2$) formed from the reacting of the HCl with the $CaCO_3$ is recycled as at least some of the $CaCl_2$) in the hydrolyzing of the $CaCl_2$) to form the HCl and the $Ca(OH)_2$. The method can include electrolytically converting the $CO_2$ and the water into a syngas composition including carbon monoxide and hydrogen.

The method of producing a syngas composition including regenerating a used $CO_2$-capture sorbent can provide a lower-temperature and lower-energy alternative to high-temperature calcination for hydroxide-based $CO_2$ DAC solvents. Solvents like KOH and NaOH have high affinity for $CO_2$, even at low partial pressure, and offer design advantages for the massive air contactors required for large-scale $CO_2$ removal from the atmosphere. For instance, being liquid, these capture solvents can be circulated over a variety of air contactor geometries while being regenerated at a central location, thereby using the full system capacity for continuous $CO_2$ capture. However, regeneration of these solvents requires decomposition of a carbonate (commonly $CaCO_3$) which is an energy-intensive, high-temperature (900° C.) process using existing calcination techniques. This energy requirement is a significant drawback for hydroxide solvents since it results in additional emissions that must be offset by DAC system capacity to produce a net $CO_2$ reduction. Instead of high-temperature calcination, the present method of regenerating a $CO_2$-capture sorbent can decompose carbonates using a regenerable acid produced from the hydrolysis of a chloride-based regeneration solution. A comparison of the process using $CaCl_2$) brine to calcination regeneration is shown in FIG. 1.

The process of brine hydrolysis regeneration in FIG. 1 can integrate with DAC systems by using hydrochloric acid (HCl) to decompose carbonates, thus releasing captured $CO_2$ and recovering the precipitated hydroxide (e.g., $Ca[OH]_2$) to regenerate soluble hydroxide solvents such as KOH and NaOH. Hydrolysis can occur at significantly lower temperatures than calcination (e.g., 400° versus 900° C.), and it can offer a feasible way to recycle thermal energy released from $Ca(OH)_2$ formation, thus lowering the quantity of input thermal energy. Chloride compounds in the regeneration solution are not consumed and can be continually recycled.

Figure 2:
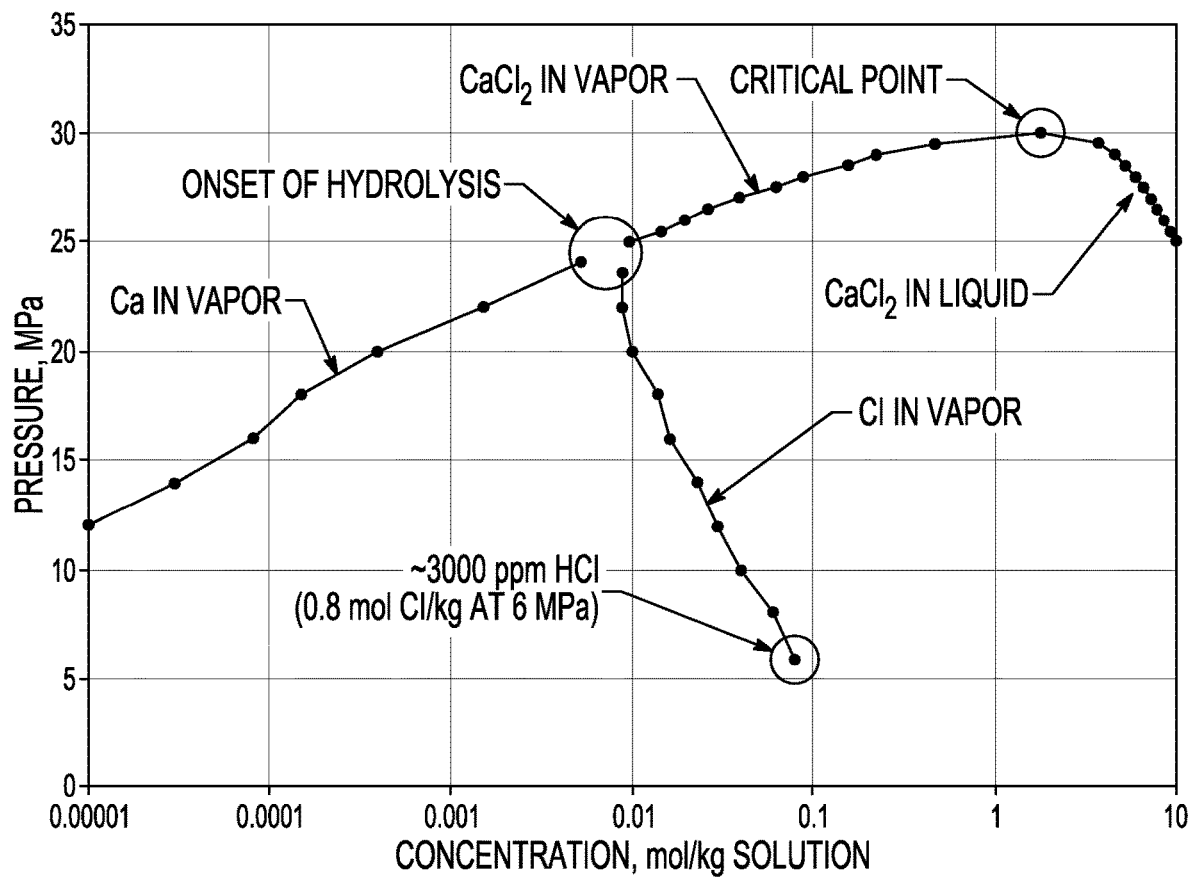
FIG. 2 illustrates pressure versus concentration for $CaCl_2$ brine hydrolysis at 400° C., in accordance with various aspects.

Brine hydrolysis can be the source of HCl used for carbonate decomposition, and it has been observed experimentally. A plot of pressure versus concentration for $CaCl_2$ brine is shown in FIG. 2, which is a plot of phase composition data for $CaCl_2$ brine near its critical point (see, Bischoff, J.; Rosenbauer, R.; Fournier, R. The Generation of HCl in the System $CaCl_2$—$H_2O$: Vapor-Liquid Relations from 380°-500° C. *Geochimica et Cosmochimica Acta* 1996, 60 (1), 7-16). As the data show, HCl is produced in significant amounts during the dynamic equilibrium above $CaCl_2$ brine held at a moderate temperature of 400° C. The hydrolysis data shown in FIG. 2 also result in corresponding $Ca(OH)_2$ left behind in the brine, some of which precipitates because of its decreasing solubility with temperature. The hydrolysis data highlighted in FIG. 2 evaluated conditions over the temperature range of 380° to 500° C. but was a study of equilibrium conditions and, by definition, did not consider the kinetics of $CaCl_2$ hydrolysis.

Referring to the brine hydrolysis regeneration process in FIG. 1, the hydrolysis reactor contains a concentrated solution of $CaCl_2$ and $H_2O$ with an acid/water phase above it. The acid/water phase can include $H_2O$ with a fraction of HCl produced as a result of brine hydrolysis; the exact amount of HCl depends on the temperature, pressure, and brine composition within the reactor. The other component from $CaCl_2$ hydrolysis, $Ca(OH)_2$, can remain in the brine and can precipitate because of its decreasing solubility with temperature. At equilibrium, the amount of $CaCl_2$ hydrolysis can be stable, but in the brine hydrolysis regeneration scheme, HCl-containing vapor can be reacted with $CaCO_3$ from causticization of a DAC solvent. This HCl consumption along with $Ca(OH)_2$ precipitation can shift the reaction toward continued hydrolysis. The decomposition of $CaCO_3$ can release a stream of captured $CO_2$ and can reproduce the $CaCl_2$ salt to complete the cycle.

Some indication of the minimum theoretical energy requirements can be gained by considering their standard heat of reaction. Table 1 compares the reaction energies for brine hydrolysis regeneration and the existing method using calcination and lime slaking; these pathways correspond to the alternatives shown in FIG. 1. Summing the reaction energies for both pathways gives the same net endothermic energy of +113 kJ/mol $CO_2$, which is a thermodynamic necessity since all inputs and outputs at the process boundary are assumed to be identical. In practice, however, recovering energy between process steps is not always feasible. For instance, lime slaking is significantly exothermic, but the reaction does not proceed in the forward direction at the temperature needed for calcination (900° C.), and as a result, heat from this reaction cannot be used to offset the calcination energy requirement of +178 kJ/mol $CO_2$ (without the input of additional work).

At this point in the process, precipitated $CaCO_3$ can enter the brine hydrolysis regeneration stage where it is decomposed using HCl to release the captured $CO_2$. The resulting $CaCl_2$ salt reforms the brine used for HCl and $Ca(OH)_2$ generation.

Nominal conditions within the brine hydrolysis process have been estimated at 400° C. and 6 MPa based on the experimental data shown in FIG. 2.

While hydroxide-based solvents such as KOH and NaOH have desirable capture and engineering properties, their high regeneration energy requirements (greater than 178 kJ/mol $CO_2$ at 900° C.) necessitates the development of improved alternatives. The method of the present invention provides a practical means to approach the theoretical limit of regeneration energy (113 kJ/mol $CO_2$) at a significantly lower temperature (400° C.), thereby providing improved $CO_2$ separation performance over the options available today.

Method of Removing $CO_2$ from Water.

The method of producing the syngas composition can be used to remove $CO_2$ from water. For example, the method can further include reacting a bicarbonate salt such as $NaHCO_3$, $Mg(HCO_3)_2$, $Ca(HCO_3)_2$, $KHCO_3$, or a combination thereof, taken from any suitable water source, with the hydroxide salt to provide the metal carbonate salt that is a carbonate salt of the metal in the metal halide salt. The method can be a method of softening water. The water source can be a natural water source, such as salt water, ocean water, brackish water, fresh water, a stream, a pond, a lake, a river, or a combination thereof. The bicarbonate salt can be $Ca(HCO_3)_2$.

In some aspects, none of the hydroxide salt of the metal formed in the hydrolysis of the metal halide salt to form the hydrohalic acid and the hydroxide salt is recycled as at least

TABLE 1

| Comparison of Regeneration Pathway Energies. | | | |
| --- | --- | --- | --- |
| Existing Calcination Regeneration | | Brine Hydrolysis Regeneration | |
| Reaction | Heat of Reaction | Reaction | Heat of Reaction |
| Carbonate Calcination $CaCO_3 \rightarrow CaO + CO_2$ | +178 kJ/mol $CO_2$ | Carbonate Decomposition $CaCO_3 + 2HCl \rightarrow CaCl_2 + CO_2 + H_2O$ | −15 kJ/mol $CO_2$ |
| Lime Slaking $CaO + H_2O \rightarrow Ca(OH)_2$ | −65 kJ/mol $CO_2$ | Brine Hydrolysis $CaCl_2 + 2H_2O \rightarrow 2HCl + Ca(OH)_2$ | +128 kJ/mol $CO_2$ |

In contrast to calcination regeneration, the reactions including brine hydrolysis regeneration in Table 1 can both proceed under the same conditions of temperature and pressure, and as a result, it is theoretically possible to reduce the regeneration energy requirement from +178 kJ/mol $CO_2$ to +113 kJ/mol $CO_2$. Even if the steps of carbonate decomposition and brine hydrolysis are not combined in the same reactor, the full energy required by brine hydrolysis alone is still a significant savings compared to calcination (+128 kJ/mol $CO_2$ versus +178 kJ/mol $CO_2$) and occurs at a much lower temperature (400° C. versus 900° C.).

Figure 3:
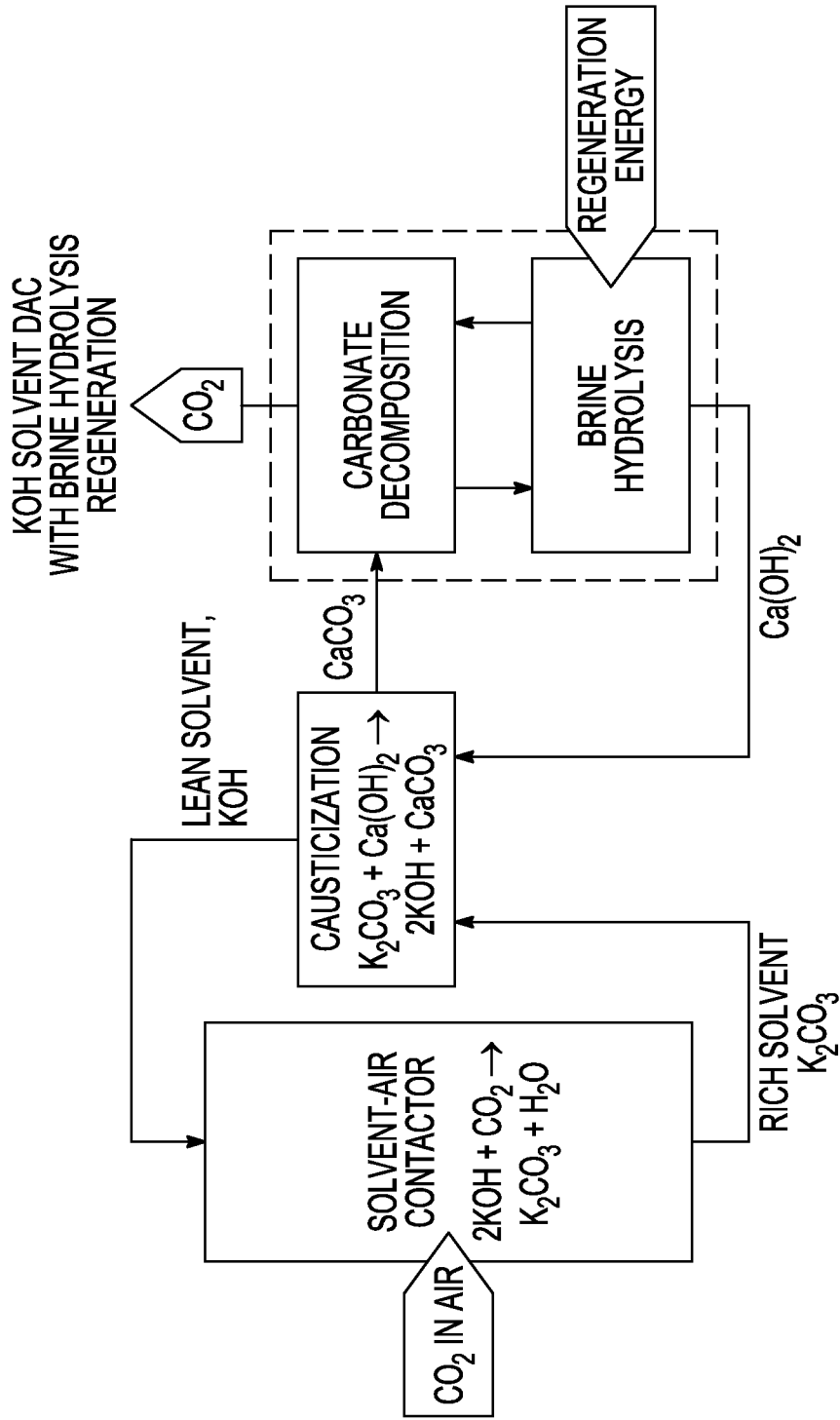
FIG. 3 illustrates a direct air capture process, in accordance with various aspects.

FIG. 3 presents a KOH solvent capture process using Ca causticization, a DAC process suitable for large-scale application. In the system, a KOH solvent contacts air and absorbs $CO_2$. Spent $CO_2$-rich solvent is then causticized using $Ca(OH)_2$ where the captured $CO_2$ is transferred from the solvent to an insoluble carbonate, $CaCO_3$ in this case. Causticization is mildly exothermic, but its primary utility is to transfer $CO_2$ from the liquid solution to a solid, thereby reducing sensible energy consumption during regeneration.

some of the hydroxide salt used in the reacting of the bicarbonate salt with the hydroxide salt. In other aspects, at least some of the hydroxide salt of the metal formed in the hydrolysis of the metal halide salt to form the hydrohalic acid and the hydroxide salt is recycled as at least some of the hydroxide salt used in the reacting of the bicarbonate salt with the hydroxide salt. For example, the hydroxide salt of the metal formed in the hydrolysis of the metal halide salt is 0.001 wt % to 100 wt % of the hydroxide salt used in the reacting of the bicarbonate salt with the hydroxide salt, or 80 wt % to 100 wt %, or less than, equal to, or greater than 0.001 wt %, 0.01, 0.1, 1, 2, 3, 4, 5, 6, 8, 10, 15, 20, 25, 30, 35, 40, 45, 50, 55, 60, 65, 70, 75, 80, 85, 90, 91, 92, 93, 94, 95, 96, 97, 98, 99, 99.9, 99.99, or 99.999 wt %, or 100 wt %.

The method of producing the syngas composition including removing $CO_2$ from water can include hydrolyzing a metal halide salt to form a hydrohalic acid and a hydroxide salt of the metal in the metal halide salt, the metal including an alkaline earth metal or an alkali metal. The method can include reacting a bicarbonate salt from a water source with the hydroxide salt, to form a carbonate salt of the metal in the metal halide salt. The method can also include reacting the hydrohalic acid with the carbonate salt, to form $CO_2$ and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt.

The method of producing the syngas composition including removing $CO_2$ from water can include hydrolyzing $CaCl_2$) to form HCl and $Ca(OH)_2$. The method can include reacting $Ca(HCO_3)_2$ from a water source with the $Ca(OH)_2$, to form $CaCO_3$. The method can include reacting the HCl with the $CaCO_3$, to form $CO_2$, water, and $CaCl_2$), wherein at least some of the $CaCl_2$) formed from the reacting of the HCl with the $CaCO_3$ is recycled as at least some of the $CaCl_2$) in the hydrolyzing of the $CaCl_2$) to form the HCl and the $Ca(OH)_2$. The method can also include electrolytically converting the $CO_2$ and the water into the syngas composition including carbon monoxide and hydrogen.

Figure 4:
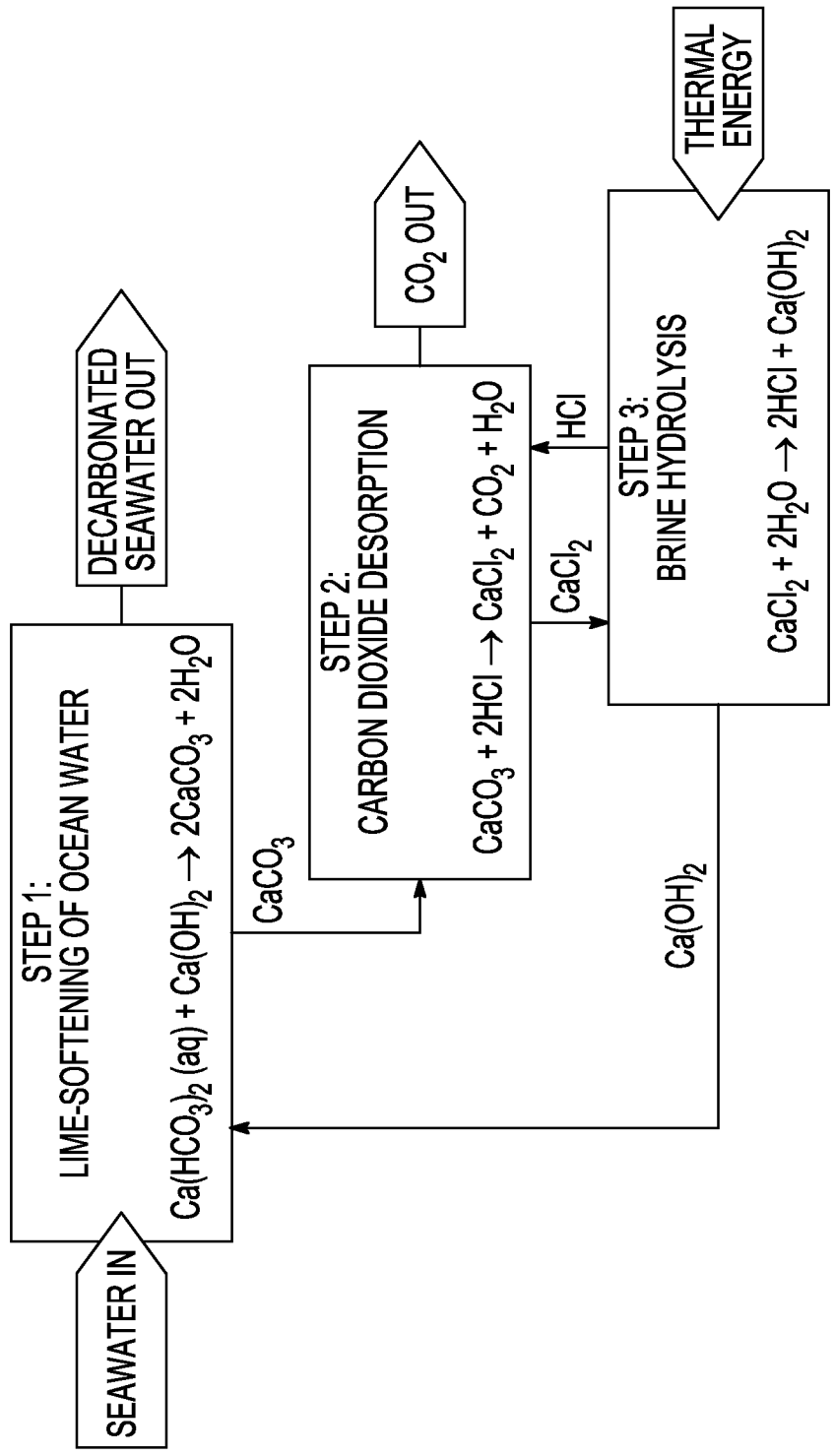
FIG. 4 illustrates a process for ocean $CO_2$ removal using hydrolytic softening, in accordance with various aspects.

An example of the method of removing $CO_2$ from water is shown in FIG. 4, which illustrates a method for removing $CO_2$ from the ocean. Advantageously, the method leverages two advantages of $CaCl_2$) splitting compared to a NaCl-based process, resulting in a transformational improvement in ocean $CO_2$ removal. Firstly, the Ca and Cl constituents of the $CaCl_2$) brine can be recycled, and when regenerated, the brine is already concentrated. This is unlike a NaCl-based process where the split NaOH and HCl constituents are released with the treated seawater and replacement NaCl brine must be reconcentrated. Secondly, the proposed method of $CaCl_2$) splitting is based on the hydrolysis of $CaCl_2$) brine, a thermochemical process where appreciable quantities of HCl are produced in the acid/water phase above a heated $CaCl_2$) brine pool. Compared to electrochemical- and/or membrane-based salt-splitting approaches, brine hydrolysis is potentially more robust and lower cost to operate. In various aspects, the method can lower the cost of ocean $CO_2$ removal to an estimated cost of $62/ton $CO_2$ or less.

Aspects of the method can address the high energy costs needed to drive ocean $CO_2$ removal. Input energy is required to convert the dominant form of $CO_2$ in the oceans, bicarbonate ion ($HCO_3^-$), to form $CO_2$ gas that can be separated for utilization or sequestration. Conceptually, this process can be shown as $HCO_3^-$ (aq)→$CO_2$ (g)+$OH^-$ (aq), which has a reaction heat of +66 kJ/mol $CO_2$. Unfortunately, real processes have not achieved this minimum level of energy consumption, and state-of-the-art approaches are estimated to require many times this amount of energy to complete the task of $CO_2$ removal. Excessive energy consumption hinders ocean $CO_2$ removal by increasing operating costs and creating additional $CO_2$ emissions that need to be offset. The method of the present invention of removing $CO_2$ from water can provide a thermochemical cycle to achieve production of $CO_2$ from bicarbonate while enabling a lower cost of energy consumption compared to what is possible today, making the concept of ocean $CO_2$ removal a more feasible tool for carbon management.

Various aspects of the method of producing the syngas composition including removing $CO_2$ from water include a process of hydrolytic softening based on salt splitting, but instead of NaCl the targeted salt can be $CaCl_2$), as shown in FIG. 4. Using $CaCl_2$) can allow for a thermochemical approach to separate the salt into acid and base, thus switching the primary form of energy input from electricity to heat. The use of $CaCl_2$) can also avoid the need to concentrate the brine prior to splitting which is an energy-intensive requirement for some NaCl-based approaches.

Hydrated lime, $Ca(OH)_2$, is used in Step 1 of FIG. 4 to remove bicarbonate ions in seawater using the familiar chemistry of lime softening: at elevated pH, bicarbonate ions are reduced to carbonate which forms solid precipitates of $CaCO_3$. The alkalinity of seawater is approximately 200 ppm (as $CaCO_3$), and cold lime softening can be expected to achieve a reduction to around 50 ppm with near stoichiometric utilization of $Ca(OH)_2$. The precipitates formed in Step 1 can be allowed to settle by gravity and are collected as a dense slurry. Softened seawater exits the process; its elevated pH to be dissipated by absorbing additional $CO_2$ from the atmosphere and mixing with untreated seawater. These mixing processes can be accelerated by mechanical means, such as to prevent harm to the local environment.

The $CaCO_3$ slurry produced from the seawater softening process in FIG. 4 can be collected and sent to a reactor where it is mixed with aqueous HCl from brine hydrolysis. The resulting spontaneous reaction (−15 kJ/mol $CO_2$) decomposes the $CaCO_3$ to liberate $CO_2$ gas and reform the $CaCl_2$) brine. In order to control the concentration of the resulting $CaCl_2$) brine, the density of the incoming $CaCO_3$ slurry can be controlled along with the concentration of the HCl solution leaving the brine hydrolysis step. Advantageously, as compared to an a NaCl-based process, the need for brine concentration before salt splitting is avoided. With a NaCl process, the split constituents of HCl and NaOH are lost to the treated seawater, and new concentrate must be continually reformed.

The $CO_2$ released during Step 2 can include associated water vapor but can otherwise be of high purity. The $CaCO_3$ slurry can act as an effective scrubbing solution for vapor-phase HCl to prevent its contamination of the $CO_2$ product. The reaction between aqueous HCl and slurry $CaCO_3$ can be conducted under pressure to produce a pressurized $CO_2$ product, thus saving gas compression energy input.

Brine hydrolysis can be a driving process behind hydrolytic softening, as shown in FIG. 4. In Step 3, the concentrated $CaCl_2$) brine, at a volume flow roughly 0.025% that of the seawater, can be hydrolyzed to form $Ca(OH)_2$ for softening and HCl to decompose the $CaCO_3$ precipitate.

As the data in FIG. 2 show, HCl is produced in significant amounts (approximately 3000 ppm) during the dynamic equilibrium above $CaCl_2$) brine held at a moderate temperature of 400° C. The hydrolysis data shown in FIG. 2 also result in corresponding $Ca(OH)_2$ left behind in the brine, some of which can precipitate because of its decreasing solubility with temperature.

In addition to the hypothesized energy savings with brine hydrolysis, other potential advantages have been identified over electrochemical approaches to salt splitting. For instance, the process chemistry is robust and can be tolerant of the other dissolved species found in seawater. Any impurities that accumulate in the process can be kept in check with a periodic blowdown of the excess seawater Ca that precipitates in addition to the Ca added from the hydrated lime. Finally, unlike electrochemical processes, there are no concerns of catalyst or membrane fouling with hydrolytic softening.

Compared to a NaCl-based process, the hydrolytic softening method described herein can be less disruptive to ocean life since it does not acidify the water which could harm sensitive organisms. As a result, hydrolytic softening can present a relatively lower environmental risk and should face fewer restrictions on its application. Regarding offshore processing costs, the simple reactor needs of hydrolytic softening make it more likely that cost projections can be met compared to a more complex process based on EDBM that requires large membrane surfaces that must be kept clean for optimal efficiency. In contrast, a floating reactor for hydrolytic softening only needs to separate seawater undergoing treatment from its surroundings and provide a collection basin (such as the ocean floor) for the precipitated carbonates. As with environmental concerns, hydrolytic softening appears to present less technical risk regarding ocean process development compared to state-of-the-art alternatives, and this feature should translate into a shorter time to market.

The method of hydrolytic water softening can be used for various purposes including ocean $CO_2$ removal and treatment of industrial waste brines. The application of treating waste brines to make them easier to recycle or to recover valuable products therefrom can include treating produced water from oil and gas development, or displaced brine from geologic $CO_2$ sequestration. Such processes could be powered by natural gas in remote areas.

EXAMPLES

Various aspects of the present invention can be better understood by reference to the following Examples which are offered by way of illustration. The present invention is not limited to the Examples given herein.

Part I. Treatment of Metal Carbonate Salt.

The reactor used in Examples 1 and 3 can decompose Ca and Mg carbonates (i.e., $CaCO_3$ and $MgCO_3$) as an alternative to conventional calcination (i.e., the direct thermal decomposition of these compounds. The reactor uses aqueous solutions of the corresponding chloride salts (i.e., $CaCl_2$ and $MgCl_2$) as a reaction intermediary to achieve carbonate decomposition at lower temperatures than those needed for direct thermal decomposition. Furthermore, the reactor converts the resulting oxide (CaO and MgO) into the corresponding hydroxide ($Ca(OH)_2$ or $Mg(OH)_2$), which is an exothermic reaction. This release of energy has the potential to offset the energy required for carbonate decomposition, a task that is virtually impossible to achieve with conventional calcination.

Figure 5:
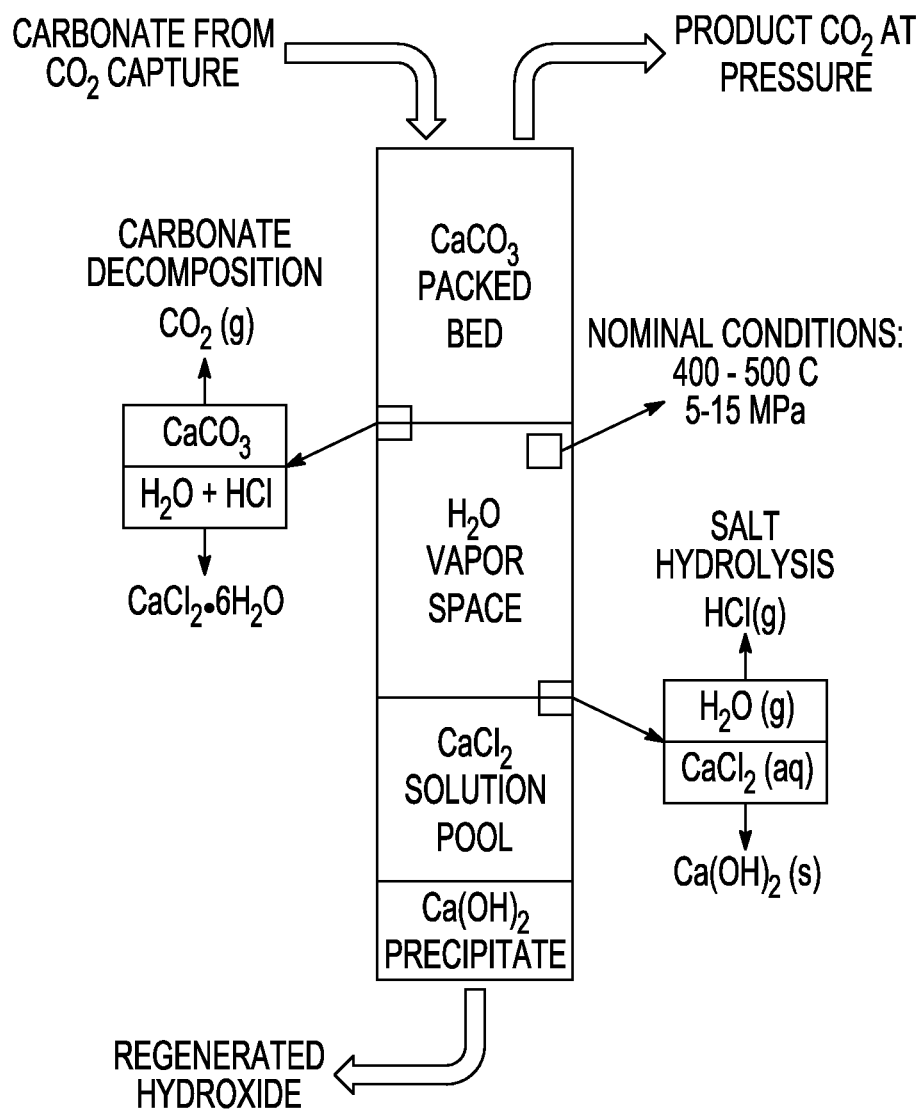
FIG. 5 illustrates a cross-section of a reactor for decomposition of $CaCO_3$, in accordance with various aspects.

The reactor is illustrated in FIG. 5, which shows the cross section of the reactor for the decomposition of $CaCO_3$ from $CO_2$-capture processes, water softening processes, and/or natural limestone. Within the sealed reactor a pool of concentrated liquid $CaCl_2$ brine resides at the bottom with a vapor phase above it. The vapor phase will consist of $H_2O$ with a small fraction of HCl gas produced as a result of $CaCl_2$ salt hydrolysis; the exact amount of HCl depends on the temperature, pressure and brine concentration within the reactor. The other component of $CaCl_2$ hydrolysis, CaO, remains in the brine and is converted to the hydroxide $Ca(OH)_2$, which can precipitate due to its low solubility. At equilibrium the degree of $CaCl_2$ hydrolysis is fixed, but in the reactor shown, solid $CaCO_3$ is suspended in the vapor phase which promotes continual hydrolysis of the salt by consuming HCl gas to reproduce $CaCl_2$ salt. $CO_2$ gas is produced during this process which can be released from the reactor along with some amount of $H_2O$ vapor. Provided the $CaCO_3$ bed depth is maintained, HCl vapor can be scrubbed from the gases exiting the reactor.

Conventional calcining of $CaCO_3$ can be represented by Reaction 1 which requires a 900° C. or higher temperature. In comparison, the proposed process using hydrolyzed $CaCl_2$ can be imagined to consist of the three steps shown in Reactions 2-4, where Reaction 2 is salt hydrolysis, Reaction 3 is the acidic decomposition of the carbonate, and Reaction 4 is hydroxide formation. Reactions 2 and 3 equate to the thermal decomposition of Reaction 1 and sum to the same theoretical heat of reaction, 178 kJ/mol $CO_2$. However, by incorporating exothermic hydroxide formation, Reaction 4, the overall alternative process has a reduced theoretical energy requirement of 112 kJ/mol $CO_2$. In addition to this 37% reduction in theoretical energy use, the alternative process has the potential to lower the required heat source temperature since Reaction 2 has been shown in the literature to occur at more moderate temperatures of 400° C.-500° C.

$CaCO_3 \rightarrow CaO + CO_2$ (+178 kJ/mol $CO_2$)  (Reaction 1)

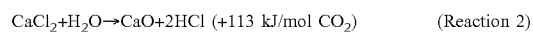
$CaCl_2 + H_2O \rightarrow CaO + 2HCl$ (+113 kJ/mol $CO_2$)  (Reaction 2)

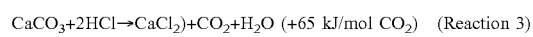
$CaCO_3 + 2HCl \rightarrow CaCl_2 + CO_2 + H_2O$ (+65 kJ/mol $CO_2$)  (Reaction 3)

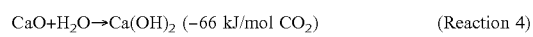
$CaO + H_2O \rightarrow Ca(OH)_2$ (−66 kJ/mol $CO_2$)  (Reaction 4)

Reactor pressure is another parameter for the process. The pressure can be selected in accordance with the temperature to maintain a distinct brine phase and another phase that includes water and the produced acid (e.g., supercritical water, such as above the brine stage), since these are required for the desired separations to take place. At the temperatures under consideration, the low pressure extreme results in solidified chloride salt in an atmosphere of $H_2O$ and HCl vapors. At the other extreme where pressure is too high, a dense phase liquid is formed with no distinct separation of hydrolysis products or $CO_2$. In this case $CO_2$ separation would be infeasible and the solid carbonate reactant (e.g. $CaCO_3$) and hydroxide product (e.g. $Ca(OH)_2$) would be mixed. Precipitation of the hydroxide on the carbonate may also block complete conversion and decrease the efficiency of sorbent recycling.

The reactor operating pressure can also be used to advantage for the production of pressurized $CO_2$ that does not require any, or as much, compression for pipeline transport or geologic sequestration. The other streams entering and exiting the reactor are solids (e.g., the carbonate and hydroxide). Conveying these materials through a pressure gradient may pose engineering challenges but since the materials are incompressible, these streams should not require excessive compression energy.

Example 1. Regeneration Solution for $CO_2$ Direct Air Capture Solvents

A laboratory-scale apparatus is used to generate the data necessary to identify the preferred regeneration solution composition from a selected set of brine chemistries, identify effective hydrolysis conditions, and provide a basis for modeling the mass and energy flows with an integrated DAC process. Capture of $CO_2$ from the atmosphere using hydroxide-based solvents like KOH and causticizing them to form $CaCO_3$ has been demonstrated elsewhere and it is not necessary to include these steps as part of this evaluation. Key processes include hydrolysis of the chloride-based brine to form HCl and precipitated $Ca(OH)_2$, decomposition of $CaCO_3$ under hydrolysis temperature and pressure conditions, and recovery of $CO_2$ gas.

Figure 6:
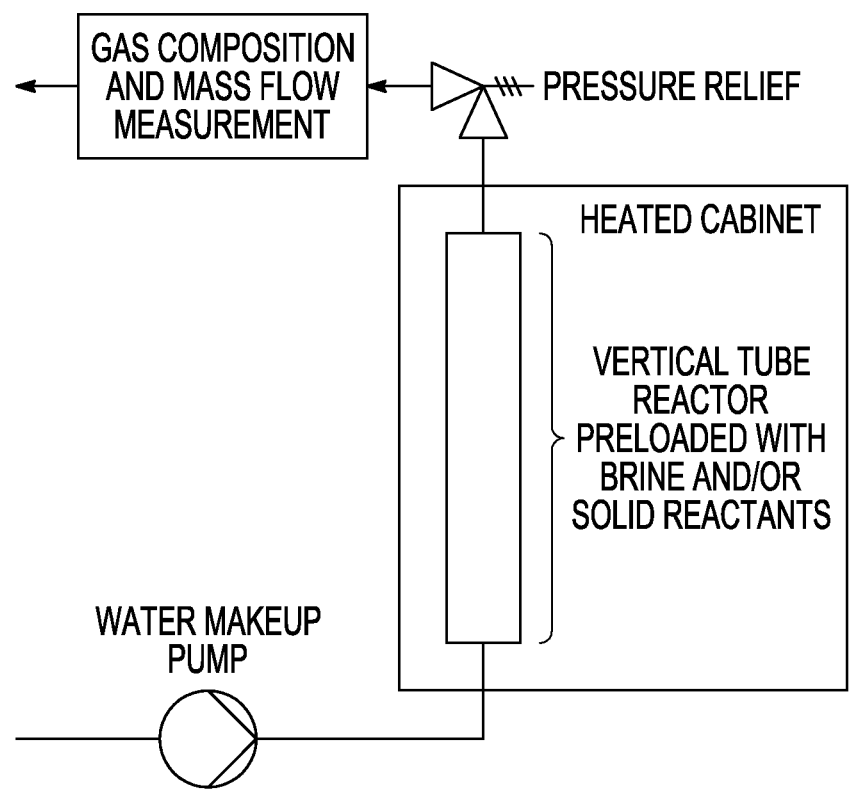
FIG. 6 illustrates an apparatus for performing hydrolytic softening of water for carbon dioxide removal, in accordance with various aspects.

The laboratory apparatus is diagrammed in FIG. 6. The apparatus includes a heated tube reactor with provisions for makeup liquid injection and an off-gas conditioning and measurement train. The reactor serves as a vessel for brine hydrolysis and as the reaction chamber for carbonate decomposition by fitting a solids basket above the liquid brine. The tubular reactor is fitted with a reacting solids basket, temperature and pressure transducers, and a vapor extraction probe. An off-gas analysis train is assembled to depressurize the vapors, allow for composition analysis, and totalize gas production.

Individual test series can have slight variations in setup and operating protocols depending on their specific objective, but all tests follow the same overall process. Prior to testing, the reactor is loaded with a predetermined quantity and composition of $CaCl_2$) as brine or solid, and for selected cases, $CaCO_3$ (without and with impurities). After heating to the test condition, vapor is extracted and its composition and flow rate recorded as a function of time. Condensed vapor samples for subsequent analysis can also be collected. The reactor operates in an open circuit mode; i.e., water vapor that would normally be recycled within the reactor is vented, and as a result, extended tests can require the addition of makeup water using a high-pressure pump. Following cooldown, the reactor is opened, and residual liquid and solid samples are collected for composition and other needed analysis.

Testing includes several evaluation stages, eventually leading to semicontinuous tests of the regeneration method. Initial tests to evaluate brine hydrolysis and carbonate decomposition are batch-operated without the addition of material inputs. Parameters including temperature over a range of 300° to 500° C. and brine composition are evaluated for their effect on hydrolysis and HCl formation. Hydrolysis is evaluated by analysis of the off-gas for HCl and the post-test analysis of recovered reactor liquids and precipitated solids. Operating pressure is constrained by temperature and brine composition and is determined for each test. Brine composition has been shown to have an effect on hydrolysis when comparing synthetic versus natural seawater, and is evaluated here in more depth by testing up to five brine chemistries to identify the preferred solution composition. All solutions are chloride-based, and one is aqueous $CaCl_2$. Following the hydrolysis evaluation, carbonate (i.e., $CaCO_3$) decomposition is evaluated at conditions suitable for brine hydrolysis to determine if this process can be incorporated within the hydrolysis reactor for simplified reactant transport and potential energy integration. Off-gas analysis is used to estimate the rate of conversion, and post-test sample recovery is used to determine conversion extent.

Testing then advances to longer-duration semicontinuous runs to evaluate mechanisms necessary for successful cycle operation. Key mechanisms include the cycling of HCl and $CaCl_2$, the precipitation and separation of $Ca(OH)_2$, the decomposition of $CaCO_3$ in a physical form it is likely to be in after causticization (i.e., precipitated from solution), the extraction of $CO_2$ product, and the ability to pass impurity species from other parts of the DAC process (e.g., KOH/ $K_2CO_3$). This is semicontinuous, where $CaCO_3$ solids are charged at the beginning of a run and product $Ca(OH)_2$ are recovered after, but $CO_2$ product vapors are withdrawn continuously, and makeup brine water is added as needed to sustain operation. Before testing, the reactor is charged with a larger quantity of the target carbonate to allow for longer, semicontinuous evaluation of regeneration cycle processes, including the precipitation and separation of $Ca(OH)_2$, the decomposition of $CaCO_3$ in a physical form it is likely to be in after causticization, and extraction of $CO_2$ and any associated vapors. Testing can identify a baseline condition that can serve as the basis for high-level process integration modeling.

Data collection includes a combination of operational data logging and posttest analysis of recovered samples. Data logging includes reactor temperature(s) and pressure and analysis of the off-gas composition and flow rate. Recovered samples from each test include residual brine liquid, precipitated solids in the brine, and residual solids left in the carbonate loading basket. Liquids undergo analysis for pH and dissolved species determination. Solids are evaluated for their chemical makeup using X-ray fluorescence and, as needed, X-ray diffraction for mineral phase identification and inspection using a scanning electron microscope.

The regeneration process is evaluated over a range of temperatures from 300° C. to 500° C. Below this range, hydrolysis diminishes because of reduced HCl vapor pressure, and above it, $Ca(OH)_2$ formation is not favored. Operating pressure is constrained by temperature and brine composition and will be determined individually for each test. Using available data, a typical operating pressure is expected to be 6 MPa.

Input solids include a target carbonate compound, $CaCO_3$, which is representative of the final capture product for DAC systems utilizing Ca causticization. Initial batch conversion tests use a purchased $CaCO_3$ reagent for test-to-test consistency, but the semicontinuous tests use $CaCO_3$ precipitated from a simulated causticization process. This precipitated material includes or is spiked with process impurities such as unconverted $Ca(OH)_2$ and carryover $KOH/K_2CO_3$ to determine their fate and demonstrate that a manageable steady state can be achieved. Ambient pollutant impurities, specifically $SO_2$ and NOR, are not be evaluated experimentally, but they will be treated using modeling to identify their likely fate and explore management options.

Chemical process modeling is used to supplement the results and extrapolate performance for a full-scale DAC. In order to estimate the potential performance of a full-scale DAC system, process modeling software Aspen Plus is used alongside experimental data to produce a complete analysis.

The proposed effort is directly relevant to the development of improved DAC systems by addressing a key barrier to commercialization for solvent DAC, i.e., the regeneration energy it requires. Cuts in regeneration energy compared to high-temperature calcination result in fewer emissions that must be offset to achieve net carbon reduction, and lowering the maximum heat source temperature expands the pool of candidate energy sources that can be applied to power large-scale DAC. Even if this approach may not result in the lowest specific separation energy or the lowest regeneration temperature compared to sorbent- or membrane-based approaches, it will still be impactful because of the engineering advantages solvents offer to the design of large-scale air contactors, in particular the ability to decouple $CO_2$ capture from regeneration. Therefore, feasible methods to reduce the energy consumption of DAC solvents can be used to implement large-scale air contactors based on solvents in the near term, but the same may not be true for sorbent- or membrane-based systems.

Example 1 Supporting Data

The process of hydrolyzing $CaCl_2$) to form HCl and $Ca(OH)_2$ was investigated experimentally to demonstrate the potential energy savings of brine hydrolysis regeneration over the conventional approach based on high-temperature calcination. The apparatus diagrammed in FIG. 6 was used to determine the degree of $CaCl_2$) hydrolysis as a function of temperature, and to experimentally determine the standard heat of reaction, which has a theoretical value of +128 kJ/mol $CO_2$ as shown in Table 1 for the brine hydrolysis reaction itself.

For the experiments, approximately 20 g of hydrated $CaCl_2$) was loaded into the vertical tube reactor of FIG. 6 and heated to temperatures over the approximate range of 250° C. to 490° C. Reactor pressure was maintained at approximately 0.1 MPa absolute, and the salt was exposed to a steam atmosphere generated from the vaporization of makeup water pumped into the heated cabinet. Steam flow was maintained by the water makeup pump and equated to a volume flow rate of approximately 3.7 Lpm at the exit conditions of the heated cabinet (i.e., 0.1 MPa and 191° C.). Hydrolysis extent was monitored by condensing the steam atmosphere exiting the reactor cabinet, and measuring condensate pH, which was correlated to HCl concentration. Periodic samples of this condensate were also collected and analyzed for calcium and chloride ions to provide confirmation of its composition.

Figure 7:
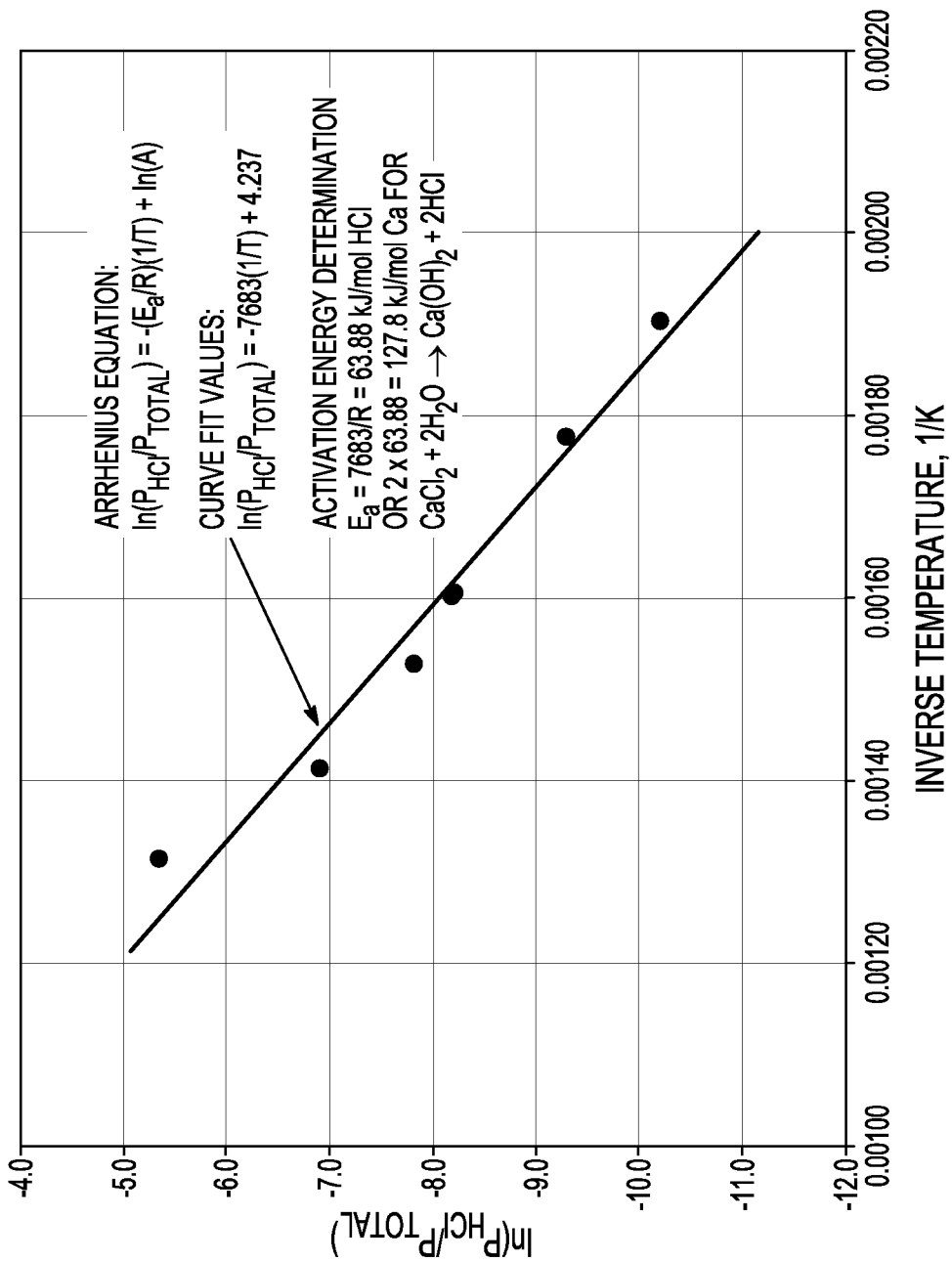
FIG. 7 illustrates an Arrhenius plot of $CaCl_2$ hydrolysis data, in accordance with various aspects.

Summary data for the $CaCl_2$) hydrolysis experiments are presented in Table 2 and in the Arrhenius plot of FIG. 7. Within experimental variability, the data clearly show a linear trend with a curve-fit slope of −7683 degrees Kelvin. Given that the slope of an Arrhenius plot is equal to the negative value of activation energy divided by the universal gas constant (8.31451 J/mol/K), the experimentally-determined activation energy was +127.8 kJ/mol Ca (or per mole $CO_2$ if discussing the entire regeneration process). This value is virtually identical to the theoretical value of $CaCl_2$ brine hydrolysis presented in Table 1, and it provides evidence of the reduced activation energy requirement of this method compared to calcination regeneration.

TABLE 2

Summary Data from $CaCl_2$ Hydrolysis Experiments.

| Reactor Pressure, MPa Absolute | Reactor Temperature, ° C. | Measured HCl Content in Gas Phase, ppmv |
| --- | --- | --- |
| 0.1 | 253 | 43 |
| 0.1 | 290 | 104 |
| 0.1 | 350 | 310 |
| 0.1 | 351 | 331 |
| 0.1 | 382 | 464 |
| 0.1 | 435 | 1140 |
| 0.1 | 487 | 5160 |

Example 2. Energy Estimation for DAC Regeneration Solution

The state point data table applicable to various solvent materials is provided in Table 3. The entries for the pure solvent, working solution, and absorption fields in Table 3 are based on a DAC system using KOH capture solvent and Ca causticization as shown in FIG. 3. Improvements from using the regeneration solution and brine hydrolysis regeneration appear under the desorption field; these values are estimated based on the minimum-pressure $CaCl_2$ hydrolysis condition presented in FIG. 2. However, it is important to note that those data were not gathered to optimize HCl production and that a wider range of temperature conditions (300° to 500° C.) and multiple brine compositions are evaluated in Example 1 to optimize DAC system integration.

TABLE 3

Preliminary state point data table.

| | Units | Measured/Estimated Performance |
| --- | --- | --- |
| Pure Solvent[a] | | |
| Molecular Weight | $mol^{-1}$ | 56.1 |
| Normal Boiling Point | C. | 1327° |
| Normal Freezing Point | C. | 405° |
| Vapor Pressure at 15° C. | bar | 0 |
| Working Solution[b] | | |
| Concentration | kg/kg | 0.10 |
| Specific Gravity (15° C./15° C.) | — | 1.09 |
| Specific Heat Capacity at STP | kJ/kg · K | 3.88 |
| Viscosity at STP | cP | 1.25 |
| Surface Tension at STP | dyn/cm | 76.5 |
| $CO_2$ Mass Transfer Rate, [$K_L$] | m/s | 0.0013 |
| $CO_2$ Reaction Rate | — | 75% over 5 s |
| Thermal Conductivity | W/(m · K) | 0.616 |
| Absorption[b] | | |
| Pressure | bar | 1 |
| Temperature | C. | 15 |
| Equilibrium $CO_2$ Loading | gmol $CO_2$/kg | 0.46 |
| Heat of Absorption | kJ/kg $CO_2$ | 2180 |
| Solution Viscosity | cP | 1.25 |
| Desorption | | |
| Pressure | bar | <50[c] |
| Temperature | C. | 300 to 350[c] |
| Equilibrium $CO_2$ Loading | gmol $CO_2$/kg | 0.002[d] |
| Heat of Desorption | kJ/kg $CO_2$ | 3800 to 5700[e] |

[a]Measured property data based on KOH as the pure solvent;
[b]Reported data based on $CO_2$ DAC with a 2M KOH solution;
[c]Projected values from extension of reported data;
[d]Projected loading assuming an optimized $CaCO_3$ conversion of 99.5%;
[e]Projected range based on similar low and high heat recuperation assumptions used for solvent DAC analysis.

The heat of desorption value in Table 3 represents an approximately 35% energy savings compared to conventional $CaCO_3$ calcination. For further comparison, recent analyses for solid DAC sorbents gave a range of 3400 to 4800 kJ/kg $CO_2$ for regeneration energy. The corresponding regeneration temperature for that sorbent analysis was assumed to be 67° to 100° C., but many engineering issues need to be overcome to realize the large-scale application of potential. The data presented in Table 3 demonstrates that brine hydrolysis regeneration can combine the desirable $CO_2$ capture and system engineering characteristics of solvent DAC with the lower energy input requirements more typical of solid sorbent processes.

Example 3. Hydrolytic Softening of Ocean Water for Carbon Dioxide Removal

Laboratory testing is used to identify effective hydrolysis conditions and provide a basis for modeling the mass and energy flows for an integrated hydrolytic softening process, as illustrated in FIG. 4. Parametric brine hydrolysis testing is performed where data will be generated regarding the extent of hydrolysis conversion at various conditions of temperature, brine composition, and vapor extraction rate. Hydrolytic lime product testing is performed, and favorable hydrolysis conditions identified during the parametric tests are repeated for extended durations to produce larger quantities of the precipitated solids (referred to as hydrolytic lime) for subsequent softening effectiveness testing.

The laboratory apparatus is diagrammed in FIG. 6; it is based around a high-temperature (1000° C. maximum) vertical tube reactor system. The apparatus includes a heated tube reactor with provisions for makeup liquid injection and an off-gas conditioning and measurement train.

For each semi-batch evaluation test, the reactor is loaded with a predetermined quantity and composition of brine. After heating to the test condition, vapor is extracted and its composition and flow rate recorded as a function of time. Composition data is determined using an online Fourier transform infrared gas analyzer that includes a calibration for HCl. The gas is also passed through an absorbing impinger solution to capture the acid gas and allow determination of a total acid quantity. For these tests, the reactor operates in an open circuit mode; i.e., water vapor that would normally be recycled within the reactor will be vented, and as a result, extended tests may require the addition of makeup water using a high-pressure pump. Following cooldown, the reactor is opened, and residual liquid and solid samples are collected for yield determination and composition analysis.

Data collection includes a combination of operational data logging and posttest analysis of recovered samples. Data logging includes reactor temperature(s) and pressure and analysis of the off-gas composition and flow rate. Recovered samples from each test include residual brine liquid and precipitated solids in the brine. Liquids undergo analysis for pH and dissolved species determination. Solids are evaluated for their chemical makeup using X-ray fluorescence and, as needed, X-ray diffraction for mineral phase identification and inspection using a scanning electron microscope.

Parametric Brine Hydrolysis Testing. Parameters including temperature and brine composition are evaluated for their effect on hydrolysis and HCl formation. Operating pressure is constrained to a feasible range bounded by too little HCl production at high pressure and crystallization of the brine if pressure is too low; this range is a function of temperature and brine composition and is determined for each test. The temperature range evaluated is 300° to 500° C., but the test range is also adapted based on test feedback in order to minimize the needed heat source temperature. Brine composition has an effect on hydrolysis when comparing synthetic versus natural seawater; as a result, pure $CaCl_2$ brine along with brine containing Mg, an expected impurity from seawater, are evaluated.

Hydrolytic Lime Product Testing. Precipitated solids that form in the hydrolysis reactor represent the material that can be used for seawater softening in a full-scale ocean $CO_2$ removal system. Favorable test conditions can be repeated and extended in time by injecting makeup solution to achieve a quasi steady-state condition. These extended runs can be used to produce sufficient quantity of hydrolytic lime product (up to gram-size quantities) for detailed composition analysis and for softening effectiveness tests using synthetic seawater solutions. These latter tests can substantiate the stoichiometry of water softening using base material from brine hydrolysis. The target base material is $Ca(OH)_2$, but could potentially include CaO, CaClOH, and unconverted $CaCl_2$).

Hydrolysis data generated is used to validate a process simulation of brine hydrolysis in Aspen Plus; this unit operation model is, in turn, used to develop a complete process for efficiently extracting HCl and $Ca(OH)_2$ products. The overall process separates HCl while recycling as much $H_2O$ as feasible to avoid wasting energy on excessive water vaporization. Another design consideration for the process is a means to recycle sensible heat between the hot products and incoming brine.

In order to estimate the potential performance of a full-scale hydrolytic softening system for seawater, process modeling software Aspen Plus is used alongside experimental data to produce a complete analysis. But the specific energy consumption (i.e., kJ/kg $CO_2$) is difficult to measure accurately an apparatus of this size. For this and other similar scenarios, chemical process models calibrated with measured experimental data is used to estimate the needed parameters. Estimates from techno-economic modeling are used to determine if a $100/ton levelized cost of $CO_2$ removal can be met.

Example 3 Supporting Data

In order to demonstrate the feasibility of applying hydrolytic softening for carbon dioxide removal from the ocean, laboratory experiments were used to measure carbonate precipitation using $Ca(OH)_2$ as the softening reagent, and to show the potential for the complete recovery of calcium that is necessary to perpetuate a cycle of regeneration and reuse. These tests used three material streams to simulate the process of carbon dioxide removal from the ocean, 1) artificial seawater, 2) softening reagent solution, and 3) seed particles to serve as nucleation sites for certain tests. Artificial seawater prepared according to ASTM D1141-98 standards (dry solids supplied by Lake Products Company, Florissant, MO), was used as the seawater source. The softening reagent solution was prepared by forming a saturated solution of $Ca(OH)_2$ in distilled water. Seed particles were composed of powdered $CaCO_3$ having a mean particle diameter of 48 μm. For tests that used seeds, they were added at a nominal loading of 10 g/L, which provided approximately 0.6 $m^2$/L of nucleation surface area.

The test procedure consisted of adjusting the pH of each seawater sample using saturated $Ca(OH)_2$ solution, adding or withholding seed particles, and agitating the solution for 24 hours of contact time. At the conclusion of 24 hours, each seawater sample was filtered to remove precipitates and the liquid was analyzed for alkalinity, calcium, and magnesium. These data are summarized in Table 4.

TABLE 4

Summary Data for Seawater Softening Tests.

| Test | Seeds Present | Starting pH After $Ca(OH)_2$ Addition | Ending Alkalinity, mg/L (as $CaCO_3$) | Ending Ca, mg/L | Ending Mg, mg/L | Calculated $CO_2$ Equivalent Removal, % | Recovered Ca to Ca Added as $Ca(OH)_2$, mol/mol |
|---|---|---|---|---|---|---|---|
| 1 | No | 8.21 | 138 | 593 | 1320 | 0.0 | NA |
| 2 | No | 8.91 | 91.4 | 566 | 1320 | 34.3 | 2.25 |

TABLE 4-continued

Summary Data for Seawater Softening Tests.

| Test | Seeds Present | Starting pH After Ca(OH)$_2$ Addition | Ending Alkalinity, mg/L (as CaCO$_3$) | Ending Ca, mg/L | Ending Mg, mg/L | Calculated CO$_2$ Equivalent Removal, % | Recovered Ca to Ca Added as Ca(OH)$_2$, mol/mol |
|---|---|---|---|---|---|---|---|
| 3 | No | 9.42 | 41.7 | 550 | 1320 | 73.6 | 1.87 |
| 4 | No | 9.84 | 42.1 | 531 | 1280 | 79.1 | 1.96 |
| 5 | No | 10.09 | 48.9 | 548 | 1240 | 79.8 | 1.54 |
| 6 | No | 10.17 | 41.7 | 581 | 1210 | 82.5 | 1.11 |
| 7 | Yes | 8.14 | 110 | 565 | 1270 | 20.7 | NA |
| 8 | Yes | 8.86 | 105 | 570 | 1310 | 23.7 | 2.06 |
| 9 | Yes | 9.28 | 38.7 | 542 | 1310 | 73.4 | 2.04 |
| 10 | Yes | 9.61 | 39.1 | 557 | 1310 | 81.9 | 1.56 |
| 11 | Yes | 9.82 | 41.7 | 560 | 1300 | 79.4 | 1.39 |
| 12 | Yes | 10.06 | 41.2 | 589 | 1290 | 83.5 | 1.04 |

Figure 8:
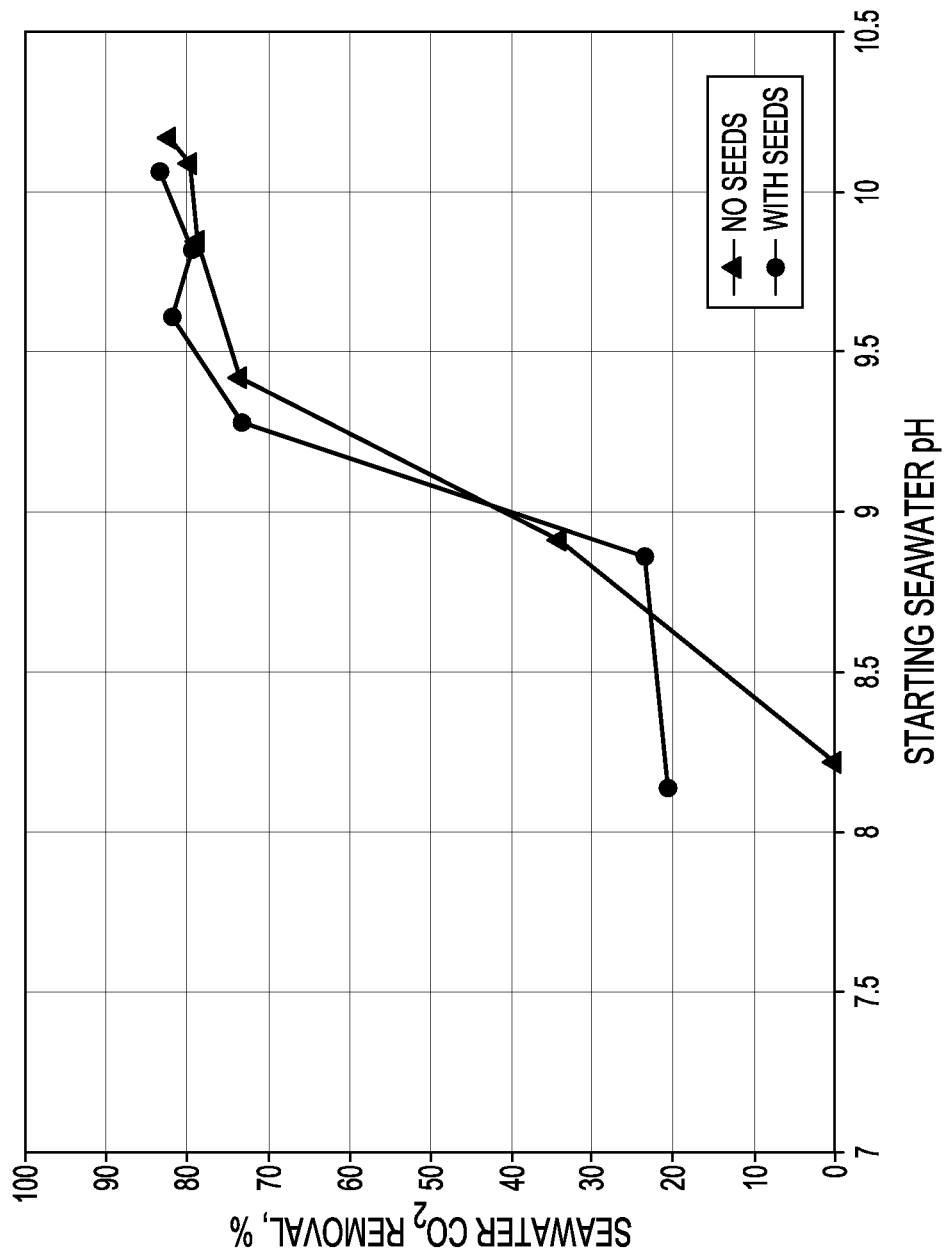
FIG. 8 illustrates percentage removal of $CO_2$ from seawater having various pH levels, in accordance with various aspects.

Test 1 in Table 4 represents the starting seawater solution and served as the basis to calculate carbon dioxide removal and to determine the amount of recovered calcium. Carbon dioxide removal results are also plotted in FIG. 8, and they indicate the potential for high efficiency, up to 73%, at adjusted pH values in the range of 9.0 to 9.5. The corresponding magnesium data in Table 4 confirm that carbon dioxide removal within this pH range occurred before any significant co-precipitation of magnesium hydroxide.

Figure 9:
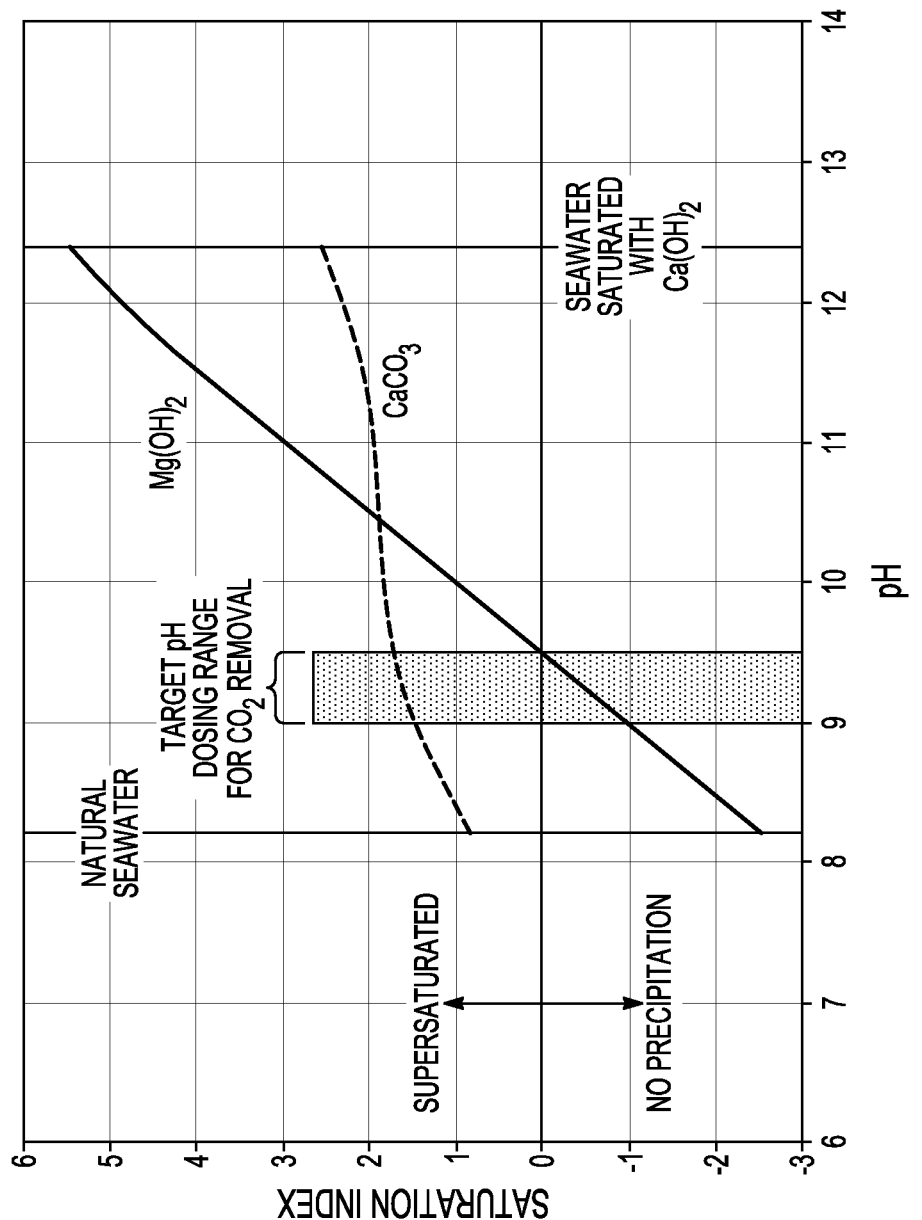
FIG. 9 illustrates calculated saturation index values for $CaCO_3$ and $Mg(OH)_2$ in seawater as a function of pH adjustment, in accordance with various aspects.

Within the pH range of approximately 9.0 to 9.5, the calcium carbonate saturation index (as calcite) approaches a maximum, but supersaturation of the unproductive and competitive precipitant magnesium hydroxide (as brucite) does not occur. This preferred range of pH adjustment for ocean carbon dioxide removal is highlighted in FIG. 9, which is a plot of calculated saturation index values for calcite and brucite.

Figure 10:
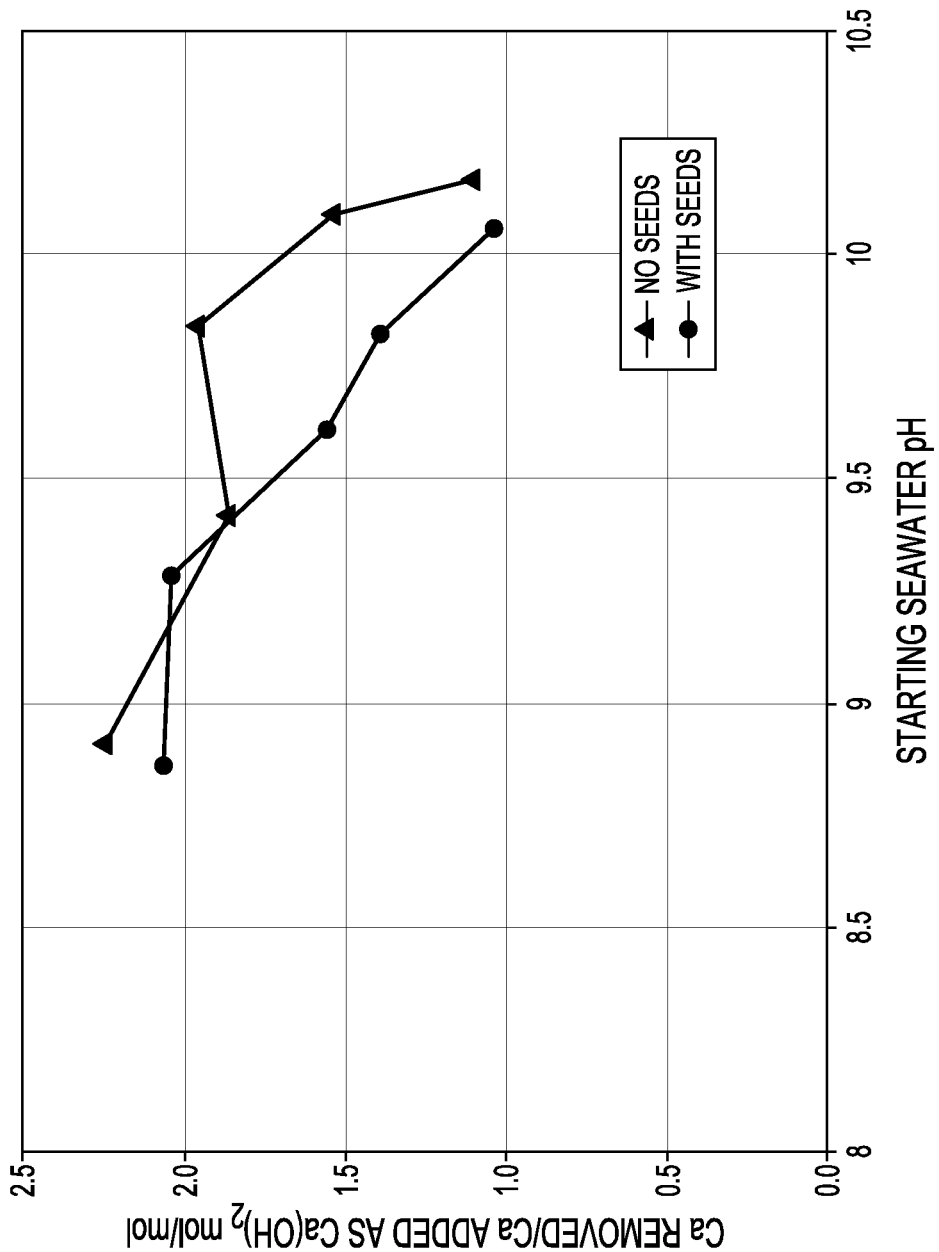
FIG. 10 illustrates the ratio of Ca removed to Ca added as $Ca(OH)_2$ for seawater having various pH levels, illustrating the experimental recovery ratio of calcium from seawater, in accordance with various aspects.

One aspect of hydrolytic softening is to operate as a closed cycle without net input of calcium. To make cyclic operation possible, the calcium used for pH adjustment as Ca(OH)$_2$ needs to be recovered as CaCO$_3$ precipitate, and recycled using the process of brine hydrolysis regeneration. To confirm that cyclic operation is possible, the experimental calcium recovery values from Table 4 are plotted in FIG. 10. Over the adjusted pH range of interest for seawater, 9.0 to 9.5, the recovery ratio has a value near two, meaning that nearly double the calcium needed for cyclic operation could potentially be recovered. This calcium recovery excess is an important operating characteristic since it will allow optimization of the precipitation stage in terms of residence time and circulation rate, and will ultimately lead to a lower cost of implementation.

Example 4. Economic Analysis of Hydrolytic Softening of Ocean Water for Carbon Dioxide Removal The key advantage offered by the proposed technology is a reduction in the energy cost required for ocean CO$_2$ removal. Energy cost savings are achieved by eliminating the need to concentrate brine prior to salt splitting and by incorporating a unique thermochemical approach for splitting. The impact of reduced energy consumption is manifested in the estimated performance metrics summarized in Table 5.

TABLE 5

Summary of performance metrics.

| Performance Metric | Target | Estimated Value |
|---|---|---|
| Levelized Cost of CO$_2$ Capture | <$100/ton CO$_2$ | $62/ton of net CO$_2$ removed |
| Second-Law Efficiency | >10% | 27% |
| Embodied Emissions (as % of life cycle captured emissions) | <5% | 0.9% |

The second-law efficiency determination was based on the minimum heat of reaction for bicarbonate ion conversion to CO$_2$ (HCO$_3^-$ (aq)→CO$_2$ (g)+OH$^-$ (aq)), which is +66 kJ/mol CO$_2$ at reference conditions. Energy consumption for hydrolytic softening was estimated to include two parts: the sensible energy needed to reach hydrolysis conditions (assumed to be 400° C.) from the reference state and the reaction energy for hydrolysis. Sensible energy consumption was estimated to be +35 kJ/mol CO$_2$ using a simple Aspen Plus model of the recuperative heating of a CaCl$_2$) brine from 20° to 400° C. with a 50° C. heat exchanger temperature approach limit. Hydrolysis energy was estimated to be +214 kJ/mol CO$_2$ by setting a 60% thermal efficiency target for CaCl$_2$) hydrolysis, Reaction 5 below, which has a theoretical reaction heat of +128 kJ/mol CO$_2$. Combined, these estimates result in a preliminary value of +249 kJ/mol CO$_2$ for hydrolytic softening; this compared to the minimum energy for CO$_2$ removal at the reference state results in a second-law efficiency estimate of 27%.

$$CaCl_2 + 2H_2O \rightarrow Ca(OH)_2 + 2HCl \quad \text{(Reaction 5)}$$

Embodied emissions were based on a nominal 1-million-ton CO$_2$ per year capture facility. An embodied emission factor of 14.6 g CO$_2$/kWhe developed for coal-fired power plants was used to estimate these emissions. The factor was converted to a thermal basis of 3.8 g CO$_2$/kWhth (assuming 45% thermal efficiency and a capacity factor of 1) and scaled for the estimated system firing rate of 163 MWth. The result was an estimate of 5890 tons CO$_2$/yr of embodied emissions for the lifetime of the project (20 years); this value was 0.9% of the estimated net CO$_2$ captured for this scenario, or 644,000 tons CO$_2$/year.

Techno-Economic Analysis.

Figure 11:
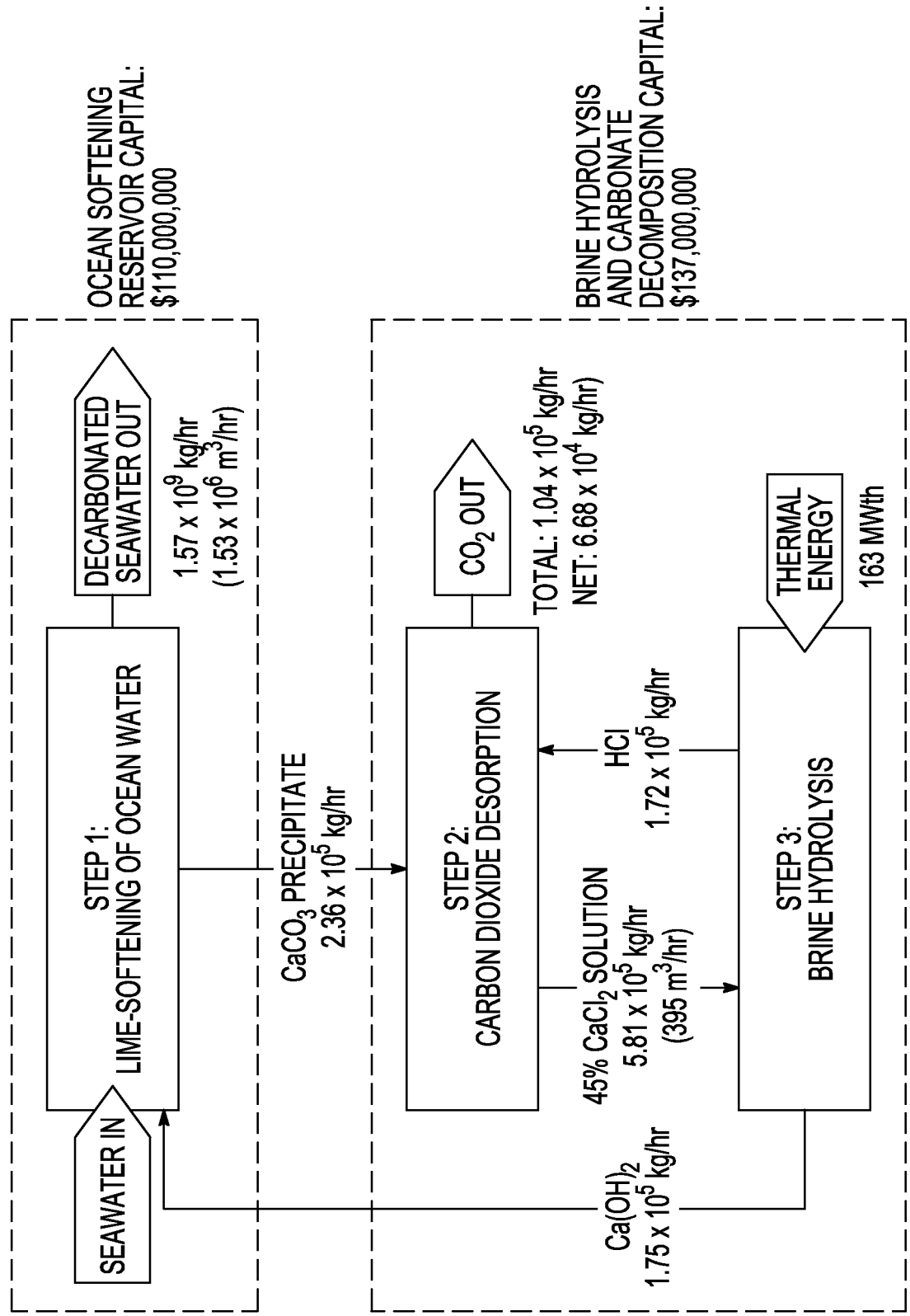
FIG. 11 illustrates process flow values used for a techno-economic assessment, in accordance with various aspects.

A preliminary cost model has been developed for a hydrolytic softening process sized for the nominal removal of 1 million tons of CO$_2$ from the ocean per year. It was estimated that with the reduced energy requirements of this concept and its use of thermal energy, a cost of $62/ton $CO_2$, appears achievable for ocean $CO_2$ removal, significantly below a $100/ton performance target. FIG. 11 illustrates process flow values used for the techno-economic assessment. Table 6 illustrates the preliminary techno-economic analysis for a hydrolytic ocean $CO_2$ removal system with 1 million tons $CO_2$ per year nominal capacity.

system perceived to have similarities to the eventual brine hydrolysis process in terms of operating temperatures and pressures and that incorporates a similar variety of unit operations (e.g., large-scale heat generation and heat transfer, emission control, solids collection and transport, and the like). Assumed cost on an electrical output basis was $2100/kWe or $840/kWth on a thermal input basis.

TABLE 6

Preliminary Techno-Economic Analysis for a Hydrolytic Ocean $CO_2$ Removal System with 1 million tons $CO_2$ per year Nominal Capacity.

| Item | Basis | Estimated Value |
| --- | --- | --- |
| Ocean Softening Reservoir Capital | $35/$m^3$ of estimated retention volume | $110,000,000 |
| Brine Hydrolysis and Carbonate Decomposition Capital | $840/kWth of estimated heat input rate | $137,000,000 |
| System Ca(OH)$_2$ Consumption | Assumed 1:1 molar ratio of Ca(OH)$_2$ to $CO_2$ gas captured | $2.07 \times 10^{10}$ mol/yr |
| System Energy Consumption | Brine hydrolysis energy required for needed HCl rate assuming 60% thermal efficiency | 163 MWth |
| Annual Energy Cost | Natural gas at $3.43/MMBtu | $16,700,000/yr |
| Nominal $CO_2$ Removed from the Ocean | Input specification | 1,000,000 ton $CO_2$/yr |
| Annual $CO_2$ Emissions from Energy Consumption | Emissions factor of 227 g $CO_2$/kWth for natural gas | 356,000 ton $CO_2$/yr |
| Net Annual $CO_2$ Capture | Difference between capture and energy emissions | 644,000 ton $CO_2$/yr |
| Levelized Cost of Net $CO_2$ Removal | Assumed a 20-year project life, 7% annual discount rate, and zero end of life value | $62/ton $CO_2$ |

Carbonate removal rate. Determination assumed an incoming concentration of 200 ppm in seawater and a softened concentration of 50 ppm (both values given as $CaCO_3$). This range is typical of conventional softener performance and results in a seawater throughput of nearly 1.6 million $m^3$/hr for a nominal 1 million tons of $CO_2$/year. The net $CO_2$ emissions were somewhat lower in Table 6 to account for $CO_2$ associated with energy production.

Hydrated lime and HCl consumption. Determined from the stoichiometric ratio of 1 mole Ca(OH)$_2$ and HCl to separate and release 1 mole of $CO_2$ gas. In reality it is likely that closer to 2 moles of $CaCO_3$ will precipitate per mole of added Ca(OH)$_2$ because of Ca(HCO$_3$)$_2$ existing in seawater, but the production of $CO_2$ gas will be constrained by HCl availability.

Brine hydrolysis energy consumption was estimated using a hydrolysis efficiency target of 60% and a reasonable sensible heat recuperation assumption of 3800 to 5700 kJ/kg $CO_2$. The energy basis for hydrolysis was estimated to be +249 kJ/mol $CaCl_2$. These assumptions resulted in a plant heat input rate of 163 MWth for the 1-million-ton/year $CO_2$ removal rate.

Power cost was assumed to be dominated by the thermal energy for brine hydrolysis. Natural gas at $3.43/MMBtu and with a carbon intensity of 227 g $CO_2$/kWth was the energy source. To account for the $CO_2$ released from gas consumption, these emissions were deducted from the plant's nominal 1-million-ton/year capacity and the resulting cost of $CO_2$ removal was normalized on a net $CO_2$ removal basis to result in an annual cost of $16,700,000 or roughly $26 per ton of net $CO_2$.

Capital cost for solids regeneration. Capital for Steps 2 and 3 in FIG. 11 was estimated by scaling the costs for a modern supercritical coal-fired power plant, an engineered Capital cost for ocean softening. Capital for Step 1 in FIG. 11 is based on what are assumed to be existing analog structures to the floating reservoir envisioned for softening, i.e., floating cages used for large-scale ocean-based aquaculture. The key cost driver for the softener infrastructure is based on the retention time needed for lime mixing and settling of the precipitated carbonates. A typical retention time value of 2 hours was assumed; at the nominal seawater throughput this sizing criteria resulted in a 3.1 million $m^3$ enclosed volume capacity. This volume is roughly one order of magnitude larger than the largest aquaculture systems in use today, suggesting that an ocean $CO_2$ removal system would require multiple units or the development of larger systems. Costs were assumed using $35/$m^3$ of enclosed volume based on a survey of aquaculture cage designs.

Part II. Method of Making Syngas

Example 5. Hypothetical Integrated Process for Making Carbon-Neutral Offshore Methanol This Part describes a hypothetical integrated process for making carbon-neutral offshore methanol (C-NOM) where the feedstocks of atmospheric $CO_2$ and $H_2O$ are harvested from the surface layer of the ocean and renewable offshore power drives methanol synthesis. C-NOM is based on integrating 1) electric methanol synthesis (i.e., to produce "e-methanol") with 2) hydrolytic softening for the direct ocean capture of $CO_2$. Among proposed e-methanol routes, C-NOM is believed to offer significant scaling potential since it largely avoids land- or freshwater-use competition by operating and harvesting feedstock molecules offshore. The integrated C-NOM production process leverages complementary features of hydrolytic softening and e-methanol synthesis to reach an $800/tMeOH production target. Deployment of C-NOM will benefit energy and chemical product decarbonization, while increasing the resilience of local ecosystems and supporting a highly skilled workforce.

Objectives of this Phase 1 project are to evaluate the integration of hydrolytic softening and e-methanol synthesis in detail to identify an optimal configuration that results in a $800/tMeOH or lower production cost and to develop the plans necessary for future Phase 2 testing. The team will prepare the conceptual design for an integrated, laboratory-scale C-NOM system; perform preliminary techno-economic and life cycle analyses; prepare a technology maturation plan and technology gap analysis; complete an initial environmental health and safety analysis; and evaluate the societal considerations and impacts of the technology.

Description of Proposed Technology and Applicability to Objectives and Success Metrics.

The objective of is to produce carbon-neutral methanol using carbon-free hydrogen and atmospheric carbon dioxide provided by direct capture from the atmosphere while targeting a production cost of $800/tMeOH or less. The proposed process for C-NOM aligns with that objective by producing methanol using 1) hydrogen made carbon-free using a combination of low-carbon renewable power input and by sequestering a stream of negative emissions $CO_2$ to offset the remaining carbon footprint and 2) atmospheric $CO_2$ absorbed in the surface layer of the ocean and removed using a direct ocean capture (DOC) process. C-NOM is predicted to reach the $800/tMeOH production target by integrating the material and energy needs of e-methanol synthesis with hydrolytic softening DOC.

Process Description and Chemistry. A process diagram for C-NOM is presented in FIG. 12 with the reactions for each process step summarized in Table 7. C-NOM production begins with the precipitation softening of seawater, where absorbed atmospheric $CO_2$, present primarily as bicarbonate in the ocean (—$HCO_3$), is captured as calcium carbonate ($CaCO_3$) from the addition of hydrated lime ($Ca[OH]2$). This step removes $CO_2$ (as bicarbonate) from the water and replaces it with hydroxide ion (—OH) which primes the seawater to reabsorb more atmospheric $CO_2$.

Figure 12:
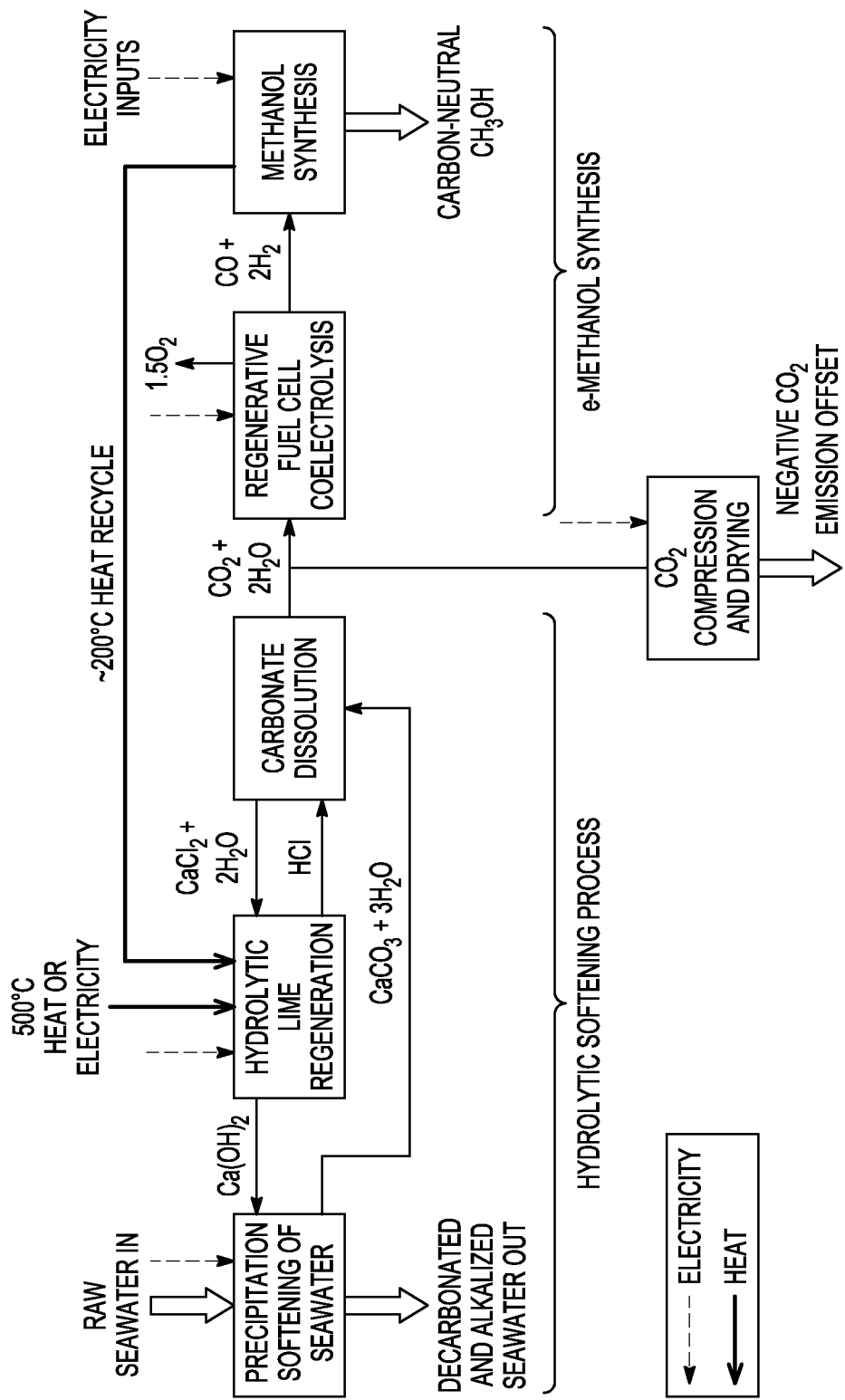
FIG. 12 illustrates an integrated process for making carbon-neutral offshore methanol (C-NOM), in accordance with various aspects.

The next steps in FIG. 12 are hydrolytic lime regeneration and carbonate dissolution. In lime regeneration, calcium chloride ($CaCl_2$)) produced within the carbonate dissolution step is hydrolyzed at 500° C. to form hydrochloric acid (HCl) and dissolved calcium hydroxide. The latter product is used for precipitation softening while the hydrochloric acid is used in the carbonate dissolution step to dissolve the calcium carbonate precipitates, releasing $CO_2$ gas and forming the intermediate neutralization salt, calcium chloride. Dissolution releases $CO_2$ gas in an atmosphere of water vapor that is evaporated from excess seawater carried in with the precipitates. This mixed $CO_2$ and $H_2O$ gas stream is used directly in the next step, regenerative fuel cell (RFC) coelectrolysis, where gas-phase electrolysis of both $H_2O$ and $CO_2$ produces a chemical synthesis gas consisting of $H_2$ and CO. These synthesis gas constituents are the feedstock molecules needed for the final step of catalytic methanol synthesis.

TABLE 7

Process Chemistry for C-NOM Production.

| Step | Governing Reaction |
| --- | --- |
| Precipitation Softening | —$HCO_3$ + $Ca(OH)_2$ → $CaCO_3$ + $H_2O$ + —OH |
| Hydrolytic Lime Regeneration | $CaCl_2$ + $2H_2O$ → $Ca(OH)_2$ + 2HCl |
| Carbonate Dissolution | $CaCO_3$ + 2HCl → $CaCl_2$ + $H_2O$ + $CO_2$ |
| Regenerative Fuel Cell Coelectrolysis | $CO_2$ + $H_2O$ → CO + $2H_2$ + $O_2$ |
| Methanol Synthesis | CO + $2H_2$ → $CH_3OH$ |

The overall process shown in FIG. 12 can be powered by a combination of 500° C. heat and electricity, or electricity alone by electrifying the heat demand of hydrolytic lime regeneration. Power generation introduces a source of upstream $CO_2$ emissions, and to offset them, the hydrolytic softening process is sized to collect an excess of $CO_2$ that is compressed and sent for geologic sequestration.

Figure 13:
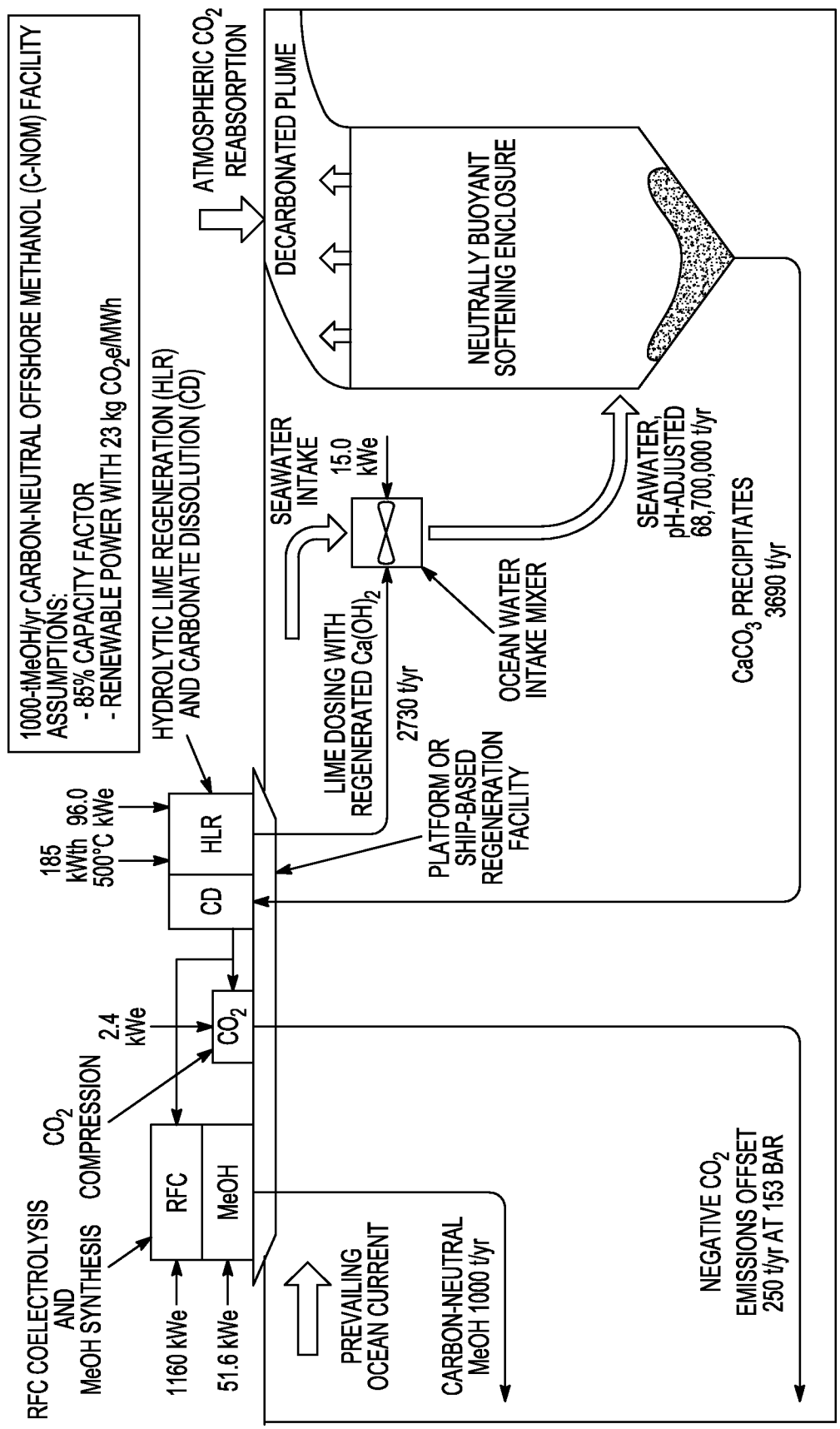
FIG. 13 illustrates a diagram showing an implementation of C-NOM, including a mass and energy balance for 1000-metric-ton-per-year methanol capacity, in accordance with various aspects.

An illustrative implementation of C-NOM is shown in FIG. 13 where the first step of precipitation softening takes place inside a neutrally buoyant softening enclosure floating in the water column. This structure would allow for contacting large volumes of seawater while retaining calcium carbonate precipitates that sink to the bottom. The remaining process steps of hydrolytic lime regeneration and e-methanol synthesis would take place at the surface on a floating or fixed platform.

Hydrolytic Softening.

Hydrolytic softening is described herein at Part I. Experimental results included measuring the reaction heat of $CaCl_2$ hydrolysis, confirming the composition of the hydrolysis products, and demonstrating the effectiveness of hydrolytic lime for seawater softening. Experimental data from Part I have been used to develop a process model for hydrolytic softening, which was used to extrapolate the mass and energy balance of C-NOM shown in FIG. 13.

Hydrolytic lime regeneration in FIGS. 12 and 13 is differentiated from the common practice of producing hydrated lime through high-temperature calcination of calcium carbonate at ~900° C., followed by slaking of the calcium oxide (CaO) with water. The key difference between hydrolytic lime regeneration and conventional calcination/slaking is that $CaCl_2$ hydrolysis yields hydrated lime directly, instead of the calcium oxide intermediary formed during calcination. This eliminates the need for slaking and saves energy by reducing the quantity of 500° C. heat by 28% compared to the amount of 900° C. heat required during calcination, i.e., 128 kJ/mol $Ca(OH)_2$ for the former versus 179 kJ/mol for the latter.

e-Methanol Synthesis.

The next C-NOM process step is coelectrolysis of the $CO_2$ and $H_2O$ vapor stream from carbonate dissolution to produce a synthesis gas mixture of CO and $H_2$ at the proper $H_2$:CO ratio for methanol synthesis (2:1). The RFC is a solid oxide electrolyzer that operates at 700° to 800° C., and it offers key benefits for this application, including 1) high conversion efficiency for electricity to synthesis gas (>80%), 2) low-cost ceramic materials as catalysts, and 3) reliable operation up to 6000 hours or more. Steam production is commonly a cost-prohibitive step for applying RFC technology since it uses gas-phase steam electrolysis. However, in this application, excess ocean water is evaporated during the hydrolysis and dissolution steps of hydrolytic softening which effectively integrates the energy burden of raising steam into the overall process, making RFC a complementary fit.

The final step of catalytic methanol synthesis is the most technically mature of the three key processes proposed for C-NOM. High-selectivity Cu—Zn catalysts have been developed, and the life cycle costs of their use are well understood. Additionally, reactor designs have been developed that allow efficient recovery of the exothermic heat of reaction in the form of 200°-250° C. steam that will be used to thermally integrate methanol synthesis with hydrolytic lime regeneration as shown in FIG. 12.

Potential Advantages.

Utilization of hybrid systems for generating carbon free hydrogen with improved long-term stability. The C-NOM approach is based on high-efficiency RFC technology that has been demonstrated for extended operating periods.

Consolidation of process operations to achieve reductions in cost. The preliminary techno-economic analysis (TEA) predicts C-NOM to reach the $800/tMeOH production target, partly by consolidating $H_2O$ electrolysis and $CO_2$ reduction into a single, high-efficiency step.

Reduction of auxiliary power by utilizing process schemes that allow heat integration. Each step of the C-NOM process has complementary thermal energy requirements with the key opportunity for thermal energy recovery being between the exothermic process of methanol synthesis and the endothermic process of hydrolytic lime regeneration.

Preliminary Conceptual Design of the Laboratory Validation System.

Under a future Phase 2 project, an integrated system for C-NOM production will be designed and operated at laboratory scale, including all steps shown in FIG. 12 with the exception of $CO_2$ compression. It is anticipated that the scale of the system will be based on a methanol production rate of ~1 tMeOH/yr or roughly 170 kg of methanol during the 2-month validation test. This production rate is 0.1% of the heat and mass balance values shown in FIG. 13, implying a 1 to 2 kWe RFC stack will be needed along with a seawater circulation rate of ~9 t/hr or 40 gpm.

State point data table values for the preliminary conceptual design are included as one of the scenarios in Table 10. A system of this scale can be used to demonstrate $CO_2$ capture and conversion to methanol; however, validating thermal efficiency claims will be challenging. As an alternative, it is proposed to limit experimental validation to conversion rates, extended term performance, and measured energy requirements, but then evaluate thermal efficiency with complementary process modeling using Aspen Plus or a similar modeling tool.

Technology Competitive Assessment.

Two pathways are available for producing carbon-neutral methanol: 1) converting biomass feedstocks into bio-methanol and 2) creating e-methanol using negative emission $CO_2$ and supplying energy from low-carbon power sources. Most carbon-neutral methanol produced today is bio-methanol, and the technology could be considered mature. As with other biomass-based energy sources, the maximum potential of bio-methanol is limited by the cost, availability, and distribution of feedstocks (e.g., municipal, agricultural, or forest wastes) and by competition for the resources needed to produce them (e.g., arable land and water). Without breakthroughs in the production of convertible biomass like, perhaps, offshore algae farming, this route to carbon-neutral methanol will face fundamental limitations to the amount of fossil methanol it could displace.

E-methanol routes, on the other hand, can potentially avoid some of the fundamental limitations faced by bio-methanol production to result in greater displacement of fossil methanol. Among the e-methanol routes, C-NOM is believed to offer significant scaling potential since it largely avoids land- or water-use competition. Water use is a criticism of direct air capture plants since the processes can lose moisture to the atmosphere under dry conditions. In addition, methanol synthesis is a water consumer since each metric ton of methanol requires 1.4 $tCO_2$ and 1.1 $tH_2O$. C-NOM negates water as a constraint since $H_2O$ is harvested along with the precipitates of calcium carbonate from the ocean.

Relevance of the Proposed Technology.

The C-NOM process is an integrated process that harvests carbon-neutral $CO_2$ and uses it to synthesize methanol with carbon-free hydrogen. The experimental data in Part I shows the concept for $CO_2$ capture to be technically viable. The oceans represent a mostly untapped resource for renewable power generation, and C-NOM can be a complementary fit to concentrate, store, and economically transport that energy to shore.

Adequacy of the Preliminary TEA and LCA to Meet Objectives.

Preliminary mass and energy balance values for a reference plant size of 1000 tMeOH/yr are presented in FIG. 13. These estimates are based on 1) experimentally based process modeling of hydrolytic softening from Part I; 2) RFC performance on advertised specifications; and 3) methanol synthesis performance from selected references on small-scale, syngas-based methanol from biomass and stranded natural gas resources.

Preliminary TEA results are shown in Table 8 along with calculation assumptions. As shown, the more carbon intense national grid scenario results in increased costs associated with offsetting energy emissions and hydrolytic softening plant size. As a result, production costs for the national grid scenario were higher than the $800/tMeOH target for both required power cost assumptions. However, the reduced carbon intensity of renewable power resulted in a lower power input and a smaller hydrolytic softening unit, leading to production values that reach the target.

TABLE 8

Preliminary TEA Results for 1000-tMeOH/yr C-NOM Reference Plant.

| TEA Parameter | National Grid Carbon Intensity, 450 kg $CO_2$e/MWh | Renewable Power Carbon Intensity, 23 kg/$CO_2$e/MWh | Calculation Assumptions |
|---|---|---|---|
| Levelized Inputs, $/tMeOH | | | |
| Total Input Energy Basis, MWe | $746 to $1344 ($25 to $45/MWh) | $282 to $507 ($25 to $45/MWh) | Combined thermal and electrical power requirements assuming 85% plant capacity factor |

TABLE 8-continued

Preliminary TEA Results for 1000-tMeOH/yr C-NOM Reference Plant.

| TEA Parameter | National Grid Carbon Intensity, 450 kg $CO_2$e/MWh | Renewable Power Carbon Intensity, 23 kg/$CO_2$e/MWh | Calculation Assumptions |
|---|---|---|---|
| Sequestration Charge for Negative Emissions $CO_2$ | $133 | $3 | Assumed $10/t$CO_2$ |
| Hydrolytic Softening Capital* | $676 | $75 | $650/t$CO_2$/yr capacity, based on TEA modeling under previous ARPA-E project |
| RFC Capital* | $190 | $190 | $2300/kW of input power |
| Methanol Synthesis Capital* | $78 | $78 | $1100/tMeOH/yr for small-scale production |
| Fixed Operations and Maintenance | $333 | $121 | 2.5% of total capital per year |
| Levelized Outputs, $/tMeOH | | | |
| Preliminary Levelized Cost of C-NOM Production, $/tMeOH | $2750 | $974 | $45/MWh power cost, DOE cost target for floating offshore wind |
| | $2160 | $748 | $25/MWh power cost, cost today for optimally sited wind resources |

*First-year capital charges determined using a 0.071 capital recovery factor that assumed a 25-year life at 5% discount rate.

Complementary to the preliminary TEA, results of a preliminary cradle-to-gate life cycle analysis (LCA) for the mass and energy streams of C-NOM are summarized in Table 9. Both scenarios in Table 9 produce the same quantity of carbon-neutral MeOH product, and as the carbon intensity of the energy source decreases from left to right, so does the input power requirement and the magnitude of the $CO_2$ sequestration stream.

TABLE 9

Preliminary LCA Results for 1000-tMeOH/yr C-NOM Reference Plant.

| | Units | Combined Heat and Electricity from National Grid, 450 kg $CO_2$e/MWh | Combined Heat and Electricity from Renewables, 23 kg $CO_2$e/MWh |
|---|---|---|---|
| Methanol Production | tMeOH/yr | 1000 | 1000 |
| Total Power Input | MW | 3.96 | 1.46 |
| $CO_2$e in Methanol | t$CO_2$e/yr | 1370 | 1370 |
| Total Power Emissions | t$CO_2$e/yr | 13,300 | 250 |
| Negative $CO_2$ Uptake | t$CO_2$/yr | 14,600 | 1620 |
| $CO_2$ to Sequestration | t$CO_2$/yr | 13,300 | 250 |

Thoroughness and Completeness of the State Point Data Table.

Preliminary state point data tables have been completed for the carbon capture process in Table 10 and the conversion of $CO_2$ to methanol in Table 11. Table 10 compares three system sizes, the first is based on the measured performance of the small laboratory proof-of-concept testing for hydrolytic lime regeneration from Part I. The other two scenarios are estimates for continuous processes scaled up to the planned size of the Phase 2 laboratory validation system and a full-scale 1000-tMeOH/yr system.

Calculation notes for Table 10 include the following items:

Scale. Measured value based on laboratory-scale, hydrolysis proof-of-concept reactor with an equivalent capacity of roughly 0.6 g/hr of $CO_2$. Projected performance range based on the capacity needed to produce 1 t/yr (validation scale) and 1000 t/yr (full-scale) of carbon-neutral methanol assuming both low carbon (23 kg $CO_2$e/MWh) and high carbon (450 kg $CO_2$e/MWh) energy.

Total Thermal Energy Requirements. Measured performance is based on the measured reaction heat of 128 kJ/mol $CO_2$. Projected heat values includes estimates for the sensible heat loss in a continuous system.

Required Temperature of Thermal Energy. Measured value range based on experiments; projected performance assumes operation at the maximum end of the range.

Total Electricity Energy Requirements. Electrical energy measurements were not meaningful at the scale of the proof-of-concept tests. Proposed electrical use is based on a process model developed for hydrolytic softening.

Volumetric Productivity. Values were based on the quantity of $CO_2$ removed per unit volume of seawater for the duration of the softener residence time. Measured value represents maximum capture at a long residence time while the projected values are based on optimal throughput, i.e., less capture efficiency but shorter residence time.

Carbon Capture Efficiency. Efficiency was determined by comparing the measured quantity of $CO_2$ precipitated as carbonate from seawater to the total amount of $CO_2$ in seawater as either carbonate or bicarbonate ions. The measured lab-scale trend was used as the basis for both the measured and the projected values.

Pressure Drop. Estimate to flow the desired quantity of seawater through a full-scale softening vessel. This value was not applicable to the laboratory system since it was a batch operation.

$CO_2$ Storage Option. This parameter is only relevant to the full-scale projected performance where geologic sequestration was assumed.

Distance to $CO_2$ Storage Option. This parameter is only relevant to the full-scale projected performance where it was assumed that initial deployments of the technology would take place on repurposed oil and gas platforms proximate to a sequestration well.

TABLE 10

State Point Data for $CO_2$ Capture System.

| | Units | Measured Proof of Concept | Projected Phase 2 Laboratory Validation | Projected Full-Scale Performance |
|---|---|---|---|---|
| Overall Process | | | | |
| Scale | tonne $CO_2$(net)/year | 0.005 | 1.6 to 15 | 1620 to 14,600 |
| Total Thermal Energy Requirements | GJ/tonne $CO_2$(net) | 2.93 | 3.06 | 3.06 |
| Required Temperature of Thermal Energy | °C. | 475-500 | 500 | 500 |
| Total Electricity Energy Requirements | GJ/tonne $CO_2$(net) | NA | 2.09 | 2.09 |
| Volumetric Productivity | gmol $CO_2$(net)/$m^3$ capture media/hr | 2.3 | 5.9 | 5.9 |
| Carbon Capture Efficiency (single pass) | % | 76% | 50% | 50% |
| Pressure Drop | Pa | NA | 104,000 Proposed/estimated | 104,000 |
| $CO_2$ Storage Option | — | NA | NA | Geologic sequestration |
| Distance to $CO_2$ Storage Option | miles | NA | NA | Within 10-mile radius |

TABLE 11

SPDT for Methanol Synthesis Portion of C-NOM.

| | Units | Measured/Current Performance | Projected/Target Performance |
|---|---|---|---|
| Synthesis Pathway Steps | | | |
| Step 1 | $mol^{-1}$ | $CO_2 + 2H_2O = CO + 2H_2 + 1.5O_2$ | |
| Step 2 | $mol^{-1}$ | $CO + 2H_2 = CH_3OH$ | |
| Reaction Thermodynamics | | | |
| Reaction | | Step 1: electrochemical | |
| | | Step 2: thermochemical | |
| $\Delta H^0_{rxn}$ | kJ/mol | Step 1: +767 $CO_2$ | |
| | | Step 2: −90.7 $CH_3OH$ | |
| $\Delta G^0_{rxn}$ | kJ/mol | Step 1: +714 $CO_2$ | |
| | | Step 2: −24.3 $CH_3OH$ | |
| Conditions | | | |
| $CO_2$ Source | | Biomass feedstock for bio-methanol | Atmospheric $CO_2$ taken from the ocean |
| Catalyst | | Step 2: Cu—Zn | Step 2: Cu—Zn |
| Pressure | bar | Step 1: 1 | Step 1: 1 |
| | | Step 2: ~55 | Step 2: ~55 |
| $CO_2$ Partial Pressure | bar | Step 1: ~0.33 | Step 1: ~0.33 |
| | | Step 2: ~6 | Step 2: ~6 |
| Temperature | °C. | Step 1: ~750-850 | Step 1: ~750-850 |
| | | Step 2: ~230-300 | Step 2: ~230-300 |
| Performance | | | |
| Nominal Residence Time | sec | <1 | <1 |
| Selectivity to Desired Product | % | 99.5 | 99.5 |

TABLE 11-continued

SPDT for Methanol Synthesis Portion of C-NOM.

| | Units | Measured/Current Performance | Projected/Target Performance |
|---|---|---|---|
| Product Composition | | | |
| Desired Product | mol % | $CH_3OH$ | $CH_3OH$ |
| Unwanted By-Product | mol % | $H_2O$ | $H_2O$ |

The state point data table (SPDT) for the production of value-added methanol from captured $CO_2$ is presented in Table 11. Measured and projected values are based on literature sources for the individual processes of RFC coelectrolysis and methanol synthesis. The results are similar since advancements within the process steps are not targeted; instead, the novelty of the proposed project is in integrating these processes together with negative emission $CO_2$.

Quality and Completeness of the Market Assessment and $CO_2$ Mitigation Potential.

Methanol is in many ways an ideal energy carrier to integrate with existing U.S. infrastructure since it is already a widely produced chemical with an established market that includes major uses as a fuel and chemical feedstock. The existing U.S. market size for methanol is over 8 Mt MeOH/yr, and between 2020 and 2022, prices ranged from $400 to $660/t MeOH. TEA projections of ~$800/tMeOH production cost for C-NOM is above the recent commodity price range; however, C-NOM would sell at a premium since it would qualify for renewable credits and other carbon-free incentives and mandates. Growth in the North American renewable methanol market is estimated to have a CAGR (compound annual growth rate) of between 4% and 8%. Most renewable methanol today is derived from biomass sources, which are anticipated to face constraints in resource availability that will drive demand for noncompetitive methanol production routes like the proposed C-NOM concept.

Transportation costs for C-NOM will impact the revenue potential of the product, but existing transport networks in the Gulf of Mexico region can be leveraged for efficient methanol transport to this market, which is 65% of the U.S. total. C-NOM development off either the U.S. West or East Coasts may not have equivalent infrastructure to leverage, but these locations could be uniquely positioned to service important export markets. For instance, the majority of the world's methanol production is consumed in southeast Asia, and carbon-neutral fuel incentives are currently driving demand in the EU. Beyond exports, offshore production might also serve the growing demand for carbon-neutral transportation fuel in the shipping industry, a goal of the U.S.-Norway Green Shipping Challenge announced at COP 27 on Nov. 7, 2022.

Each metric ton of fossil-based methanol displaced by carbon-neutral methanol would prevent not only the direct emission of 1.37 $tCO_2$ from methanol combustion, but also another ~1.9 $tCO_2e$ from producing 1 metric ton of methanol from natural gas, currently the dominant method of production in the U.S. Therefore, each GW of offshore wind production dedicated to methanol production could result in approximately 0.44 Mt MeOH/yr (assuming 55% annual wind capacity factor) or nearly 5% of current (2020) U.S. conventional methanol production capacity to avert nearly 1.4 $MtCO_2e$ in associated emissions. For context, the U.S. Bureau of Ocean Energy Management recently estimated the technical potential for offshore wind power in the Gulf of Mexico to be over 500 GW.

Degree that Captured $CO_2$ is Utilized in the Product.

Results of the preliminary LCA have been used to evaluate the carbon flows predicted for C-NOM, and Table 12 is a results summary. Like the preliminary LCA, carbon utilization increases as the amount of energy-related emissions decrease from left to right.

TABLE 12

Carbon Flow Summaries for Various Energy Sources.

| | Combined Heat and Electricity from National Grid, 450 kg $CO_2e$/MWh | Combined Heat and Electricity from Renewables, 23 kg $CO_2e$/MWh |
|---|---|---|
| Total C Uptake | 100% | 100% |
| C to Sequestration | 91% | 15% |
| C to Methanol | 9% | 85% |

The terms and expressions that have been employed are used as terms of description and not of limitation, and there is no intention in the use of such terms and expressions of excluding any equivalents of the features shown and described or portions thereof, but it is recognized that various modifications are possible within the scope of the aspects of the present invention. Thus, it should be understood that although the present invention has been specifically disclosed by specific aspects and optional features, modification and variation of the concepts herein disclosed may be resorted to by those of ordinary skill in the art, and that such modifications and variations are considered to be within the scope of aspects of the present invention.

Exemplary Aspects.

The following exemplary aspects are provided, the numbering of which is not to be construed as designating levels of importance:

Aspect 1 provides a method of forming a syngas composition, the method comprising:
  hydrolyzing a metal halide salt to form a hydrohalic acid and a hydroxide salt of the metal in the metal halide salt, the metal comprising an alkaline earth metal or an alkali metal;
  reacting the hydrohalic acid with a metal carbonate salt, wherein the metal carbonate salt is a carbonate salt of the alkaline earth metal or alkali metal, to form $CO_2$, water, and the metal halide salt, wherein at least some of the metal halide salt formed from the reacting of the hydrohalic acid with the metal carbonate salt is recycled as at least some of the metal halide salt in the hydrolyzing of the metal halide salt to form the hydrohalic acid and the hydroxide salt; and electrolytically converting the $CO_2$ and the water into the syngas composition comprising carbon monoxide and hydrogen.

Aspect 2 provides the method of Aspect 1, wherein the metal carbonate salt is $BeCO_3$, $MgCO_3$, $CaCO_3$, $SrCO_3$, $BaCO_3$, $RaCO_3$, $Li_2CO_3$, $Na_2CO_3$, $K_2CO_3$, $Rb_2CO_3$, $Cs_2CO_3$, $Fr_2CO_3$, or a combination thereof.

Aspect 3 provides the method of any one of Aspects 1-2, wherein the metal carbonate salt is $CaCO_3$, $MgCO_3$, or a combination thereof.

Aspect 4 provides the method of any one of Aspects 1-3, wherein the metal carbonate salt is $CaCO_3$.

Aspect 5 provides the method of Aspect 4, wherein the $CaCO_3$ is produced from a $CO_2$-capture sorbent, is a $CaCO_3$ precipitate formed from water softening, is natural limestone, or a combination thereof.

Aspect 6 provides the method of any one of Aspects 1-5, wherein the alkaline earth metal or alkali metal is beryllium, magnesium, calcium, strontium, barium, radium, lithium, sodium, potassium, rubidium, cesium, francium, or a combination thereof.

Aspect 7 provides the method of any one of Aspects 1-6, wherein the alkaline earth metal or alkali metal is magnesium, calcium, or a combination thereof.

Aspect 8 provides the method of any one of Aspects 1-7, wherein the alkaline earth metal or alkali metal is calcium.

Aspect 9 provides the method of any one of Aspects 1-8, wherein the metal halide salt is a beryllium halide salt, a magnesium halide salt, a calcium halide salt, a strontium halide salt, a barium halide salt, a radium halide salt, a lithium halide salt, a sodium halide salt, a potassium halide salt, a rubidium halide salt, a cesium halide salt, a francium halide salt, or a combination thereof.

Aspect 10 provides the method of any one of Aspects 1-9, wherein the metal halide salt is beryllium chloride, magnesium chloride, calcium chloride, strontium chloride, barium chloride, radium chloride, lithium chloride, sodium chloride, potassium chloride, rubidium chloride, cesium chloride, francium chloride, or a combination thereof.

Aspect 11 provides the method of any one of Aspects 1-10, wherein the metal halide salt is $CaCl_2$), $MgCl_2$, or a combination thereof.

Aspect 12 provides the method of any one of Aspects 1-11, wherein the metal halide salt is $CaCl_2$).

Aspect 13 provides the method of any one of Aspects 1-12, wherein the hydrohalic acid is HCl, HBr, HI, HF, or a combination thereof.

Aspect 14 provides the method of any one of Aspects 1-13, wherein the hydrohalic acid is HCl.

Aspect 15 provides the method of any one of Aspects 1-14, wherein the hydroxide salt is $Be(OH)_2$, $Mg(OH)_2$, $Ca(OH)_2$, $Sr(OH)_2$, $Ba(OH)_2$, $Ra(OH)_2$, LiOH, NaOH, KOH, RbOH, CsOH, FrOH, or a combination thereof.

Aspect 16 provides the method of any one of Aspects 1-15, wherein the hydroxide salt is $Ca(OH)_2$, $Mg(OH)_2$, or a combination thereof.

Aspect 17 provides the method of any one of Aspects 1-16, wherein the hydroxide salt is $Ca(OH)_2$.

Aspect 18 provides the method of any one of Aspects 1-17, wherein
the metal carbonate salt is $CaCO_3$,
the alkaline earth metal or alkali metal is calcium,
the metal halide salt is $CaCl_2$),
the hydrohalic acid is HCl, and
the hydroxide salt is $Ca(OH)_2$.

Aspect 19 provides the method of any one of Aspects 1-18, wherein the hydrolyzing of the metal halide salt is performed at a pressure of 0.1 MPa-100 MPa.

Aspect 20 provides the method of any one of Aspects 1-19, wherein the hydrolyzing of the metal halide salt is performed at a pressure of 3 MPa to 9 MPa.

Aspect 21 provides the method of any one of Aspects 1-20, wherein the hydrolyzing of the metal halide salt is performed at a pressure of 5-7 MPa.

Aspect 22 provides the method of any one of Aspects 1-21, wherein the hydrolyzing of the metal halide salt is performed at a temperature of room temperature to 1000° C.

Aspect 23 provides the method of any one of Aspects 1-22, wherein the hydrolyzing of the metal halide salt is performed at a temperature of 300° C. to 500° C.

Aspect 24 provides the method of any one of Aspects 1-23, wherein the hydrolyzing of the metal halide salt is performed at a temperature of 350° C. to 450° C.

Aspect 25 provides the method of any one of Aspects 1-24, wherein the hydrolyzing of the metal halide salt produces the hydrohalic acid at a molar content of 0.01% to 10%.

Aspect 26 provides the method of any one of Aspects 1-25, wherein the hydrolyzing of the metal halide salt produces the hydrohalic acid at a molar content of 0.1% to 1%.

Aspect 27 provides the method of any one of Aspects 1-26, wherein the reacting of the hydrohalic acid with the metal carbonate salt is performed at a pressure of 0.1 MPa-100 MPa.

Aspect 28 provides the method of any one of Aspects 1-27, wherein the reacting of the hydrohalic acid with the metal carbonate salt is performed at a pressure of 3 MPa to 9 MPa.

Aspect 29 provides the method of any one of Aspects 1-28, wherein the reacting of the hydrohalic acid with the metal carbonate salt is performed at a temperature of room temperature to 500° C.

Aspect 30 provides the method of any one of Aspects 1-29, wherein the reacting of the hydrohalic acid with the metal carbonate salt is performed at a temperature of 350° C. to 450° C.

Aspect 31 provides the method of any one of Aspects 1-30, wherein the metal halide salt formed from the reacting of the hydrohalic acid with the metal carbonate salt is 0.001 wt % to 100 wt % of the metal halide salt used in the hydrolyzing of the metal halide salt to form the hydrohalic acid and the hydroxide salt.

Aspect 32 provides the method of any one of Aspects 1-31, wherein the metal halide salt formed from the reacting of the hydrohalic acid with the metal carbonate salt is 80 wt % to 100 wt % of the metal halide salt used in the hydrolyzing of the metal halide salt to form the hydrohalic acid and the hydroxide salt.

Aspect 33 provides the method of any one of Aspects 1-32, wherein the hydrolyzing of the metal halide salt and the reacting of the hydrohalic acid with the metal carbonate salt is performed together in a pressurized reactor.

Aspect 34 provides the method of any one of Aspects 1-33, further comprising reacting a used $CO_2$-capture sorbent with the hydroxide salt to provide the metal carbonate salt that is a carbonate salt of the metal in the metal halide salt.

Aspect 35 provides the method of Aspect 34, wherein the used $CO_2$-capture sorbent is a used hydroxide-based, ammonia-based, and/or amine-based $CO_2$-capture sorbent.

Aspect 36 provides the method of any one of Aspects 34-35, wherein the used $CO_2$-capture sorbent is derived from sorption of $CO_2$ by a hydroxide-based, ammonia-based, and/or amine-based $CO_2$-capture sorbent.

Aspect 37 provides the method of any one of Aspects 34-36, wherein the $CO_2$-capture sorbent is a used hydroxide-based $CO_2$-capture sorbent.

Aspect 38 provides the method of any one of Aspects 34-37, wherein the used $CO_2$-capture sorbent is $Ca(HCO_3)_2$, $Mg(HCO_3)_2$, $K_2CO_3$, $Na_2CO_3$, or a combination thereof.

Aspect 39 provides the method of any one of Aspects 34-38, wherein the reacting of the used $CO_2$-capture sorbent with the hydroxide salt to provide the metal carbonate salt is performed at a pressure of 0.01 MPa to 10 MPa.

Aspect 40 provides the method of any one of Aspects 34-39, wherein the reacting of the used $CO_2$-capture sorbent with the hydroxide salt to provide the metal carbonate salt is performed at a pressure of about 0.05 MPa to 0.2 MPa.

Aspect 41 provides the method of any one of Aspects 34-40, wherein the reacting of the used $CO_2$-capture sorbent with the hydroxide salt to provide the metal carbonate salt is performed at a temperature of room temperature to 350° C.

Aspect 42 provides the method of any one of Aspects 34-41, wherein the reacting of the used $CO_2$-capture sorbent with the hydroxide salt to provide the metal carbonate salt is performed at a temperature of 50° C. to 150° C.

Aspect 43 provides the method of any one of Aspects 34-42, further comprising contacting a $CO_2$-capture sorbent with $CO_2$ to form the used $CO_2$-capture sorbent.

Aspect 44 provides the method of any one of Aspects 34-43, further comprising contacting $Ca(OH)_2$, $Mg(OH)_2$, KOH, and/or NaOH with $CO_2$ to form the used $CO_2$-capture sorbent.

Aspect 45 provides the method of any one of Aspects 34-44, wherein the reacting of the used $CO_2$-capture sorbent with the hydroxide salt to form the metal carbonate salt also forms an unused $CO_2$-capture sorbent.

Aspect 46 provides the method of Aspect 45, wherein the unused $CO_2$-capture sorbent is $Ca(OH)_2$, $Mg(OH)_2$, KOH, and/or NaOH.

Aspect 47 provides the method of any one of Aspects 45-46, wherein the unused $CO_2$-capture sorbent is KOH and/or NaOH.

Aspect 48 provides the method of any one of Aspects 45-47, further comprising providing the unused $CO_2$-capture sorbent for $CO_2$ capture.

Aspect 49 provides the method of any one of Aspects 34-48, wherein at least some of the hydroxide salt of the metal formed in the hydrolysis of the metal halide salt to form the hydrohalic acid and the hydroxide salt is recycled as at least some of the hydroxide salt used in the reacting of the used $CO_2$-capture sorbent with the hydroxide salt.

Aspect 50 provides the method of Aspect 49, wherein the hydroxide salt of the metal formed in the hydrolysis of the metal halide salt is 0.001 wt % to 100 wt % of the hydroxide salt used in the reacting of the used $CO_2$-capture sorbent with the hydroxide salt.

Aspect 51 provides the method of any one of Aspects 49-50, wherein the hydroxide salt of the metal formed in the hydrolysis of the metal halide salt is 80 wt % to 100 wt % of the hydroxide salt used in the reacting of the used $CO_2$-capture sorbent with the hydroxide salt.

Aspect 52 provides the method of any one of Aspects 1-51, further comprising reacting $NaHCO_3$, $Mg(HCO_3)_2$, $Ca(HCO_3)_2$, $KHCO_3$, or a combination thereof, with the hydroxide salt to provide the metal carbonate salt that is a carbonate salt of the metal in the metal halide salt.

Aspect 53 provides the method of Aspect 52, wherein the method is a method of softening water.

Aspect 54 provides the method of any one of Aspects 1-53, further comprising reacting a bicarbonate salt from a natural water source, wherein the bicarbonate salt is $NaHCO_3$, $Mg(HCO_3)_2$, $Ca(HCO_3)_2$, $KHCO_3$, or a combination thereof, with the hydroxide salt to provide the metal carbonate salt.

Aspect 55 provides the method of Aspect 54, wherein the natural water source comprises salt water, ocean water, brackish water, fresh water, a stream, a pond, a lake, a river, or a combination thereof.

Aspect 56 provides the method of any one of Aspects 54-55, wherein the bicarbonate salt is $Ca(HCO_3)_2$.

Aspect 57 provides the method of any one of Aspects 54-56, wherein at least some of the hydroxide salt of the metal formed in the hydrolysis of the metal halide salt to form the hydrohalic acid and the hydroxide salt is recycled as at least some of the hydroxide salt used in the reacting of the bicarbonate salt with the hydroxide salt.

Aspect 58 provides the method of Aspect 57, wherein the hydroxide salt of the metal formed in the hydrolysis of the metal halide salt is 0.001 wt % to 100 wt % of the hydroxide salt used in the reacting of the bicarbonate salt with the hydroxide salt.

Aspect 59 provides the method of any one of Aspects 57-58, wherein the hydroxide salt of the metal formed in the hydrolysis of the metal halide salt is 80 wt % to 100 wt % of the hydroxide salt used in the reacting of the bicarbonate salt with the hydroxide salt.

Aspect 60 provides the method of any one of Aspects 1-59, wherein the water formed during the reacting of the hydrohalic acid comprises gaseous water.

Aspect 61 provides the method of any one of Aspects 1-60, wherein the water formed during the reacting of the hydrohalic acid has a temperature of 100° C. to 500° C.

Aspect 62 provides the method of any one of Aspects 1-61, wherein the water formed during the reacting of the hydrohalic acid has a temperature of 100° C. to 150° C.

Aspect 63 provides the method of any one of Aspects 1-62, wherein 50-100 wt % of the water formed during the reacting of the hydrohalic acid is gaseous water.

Aspect 64 provides the method of any one of Aspects 1-63, wherein 90-100 wt % of the water formed during the reacting of the hydrohalic acid is gaseous water.

Aspect 65 provides the method of any one of Aspects 1-64, wherein the electrolytic conversion of the $CO_2$ and the water into the syngas composition converts 50% to 100% of the $CO_2$.

Aspect 66 provides the method of any one of Aspects 1-65, wherein the electrolytic conversion of the $CO_2$ and the water into the syngas composition converts 90% to 100% of the $CO_2$.

Aspect 67 provides the method of any one of Aspects 1-66, wherein the electrolytic conversion of the $CO_2$ and the water into the syngas composition converts 50% to 100% of the water.

Aspect 68 provides the method of any one of Aspects 1-67, wherein the electrolytic conversion of the $CO_2$ and the water into the syngas composition converts 90% to 100% of the water.

Aspect 69 provides the method of any one of Aspects 1-68, wherein carbon monoxide is 15 mol % to 40 mol % of the syngas composition.

Aspect 70 provides the method of any one of Aspects 1-69, wherein carbon monoxide is 30 mol % to 36 mol % of the syngas composition.

Aspect 71 provides the method of any one of Aspects 1-70, wherein hydrogen is 30 mol % to 80 mol % of the syngas composition.

Aspect 72 provides the method of any one of Aspects 1-71, wherein hydrogen is 60 mol % to 75 mol % of the syngas composition.

Aspect 73 provides the method of any one of Aspects 1-72, wherein the syngas composition has a molar ratio of hydrogen to carbon monoxide of 1:1 to 3.5:1.

Aspect 74 provides the method of any one of Aspects 1-73, wherein the syngas composition has a molar ratio of hydrogen to carbon monoxide of 1.9:1 to 2.1:1.

Aspect 75 provides the method of any one of Aspects 1-74, wherein the syngas composition has a concentration of $CO_2$ of 0 mol % to 20 mol %.

Aspect 76 provides the method of any one of Aspects 1-75, wherein the syngas composition has a concentration of $CO_2$ of 0 mol % to 5 mol %.

Aspect 77 provides the method of any one of Aspects 1-76, wherein the syngas composition has a concentration of water of 0 mol % to 33 mol %.

Aspect 78 provides the method of any one of Aspects 1-77, wherein the syngas composition has a concentration of water of 0 mol % to 10 mol %.

Aspect 79 provides the method of any one of Aspects 1-78, wherein the electrolytically converting the $CO_2$ and the water into the syngas composition comprises placing the $CO_2$ and/or the water into contact with an electrolytic cell.

Aspect 80 provides the method of Aspect 79, wherein the electrolytic cell comprises a reverse fuel cell, a solid oxide electrolysis cell or a molten carbonate electrolysis cell.

Aspect 81 provides the method of any one of Aspects 79-80, wherein the electrolytic cell comprises a solid oxide electrolysis cell.

Aspect 82 provides the method of Aspect 81, wherein the electrolytic cell comprises an anode, cathode, and an electrolyte, wherein at least one of the anode, cathode, and the electrolyte comprises yttria-stabilized zirconia (YSZ).

Aspect 83 provides the method of any one of Aspects 81-82, wherein the electrolytic cell comprises a cathode comprising Ni.

Aspect 84 provides the method of any one of Aspects 81-83, wherein the electrolytic cell comprises an anode comprising lithium strontium manganite (LSM).

Aspect 85 provides the method of any one of Aspects 81-84, wherein the electrolytic cell comprises an electrolyte comprising yttria-stabilized zirconia (YSZ), a cathode comprising Ni-YSZ, and an anode comprising lithium strontium manganite (LSM)-YSZ cathode.

Aspect 86 provides the method of any one of Aspects 79-85, wherein the method comprises using the electrolytic cell at a temperature of 500° C. to 1,000° C.

Aspect 87 provides the method of any one of Aspects 79-86 wherein the method comprises using the electrolytic cell at a temperature of 700° C. to 800° C.

Aspect 88 provides the method of any one of Aspects 1-87, wherein the electrolytically converting the $CO_2$ and the water into the syngas composition comprises placing the $CO_2$ into contact with a first electrolytic cell that electrolytically converts the $CO_2$ to CO, and placing the water into contact with a second electrolytic cell that electrolytically converts the $H_2O$ to $H_2$.

Aspect 89 provides the method of any one of Aspects 1-88, wherein the electrolytically converting the $CO_2$ and the water into the syngas composition comprises placing the $CO_2$ and the water into contact with an electrolytic cell that electrolytically converts the $CO_2$ to CO and that electrolytically converts the $H_2O$ to $H_2$.

Aspect 90 provides the method of any one of Aspects 1-89, wherein the method further comprises using the syngas composition as a starting material to form a product comprising ammonia, methanol, a liquid fuel, a lubricant, gasoline, an oxo alcohol, or a combination thereof.

Aspect 91 provides the method of any one of Aspects 1-90, further comprising recycling at least some exothermic heat generated by the formation of the product from the starting material in the method.

Aspect 92 provides the method of any one of Aspects 1-91, wherein recycling at least some exothermic heat generated by the formation of the product from the starting material in the method comprises supplying at least part of the generated exothermic heat to the reaction of the hydrohalic acid with the metal carbonate salt to form the metal halide salt.

Aspect 93 provides the method of any one of Aspects 1-92, wherein the method further comprises using the syngas composition as a starting material in a Fischer-Tropsch process to form one or more hydrocarbons.

Aspect 94 provides the method of any one of Aspects 1-93, wherein the method is a method of making methanol, wherein the method further comprises using the syngas composition as a starting material to form methanol.

Aspect 95 provides the method of Aspect 94, wherein forming the methanol comprises reacting the CO and the hydrogen in the presence of a catalyst to form methanol.

Aspect 96 provides the method of Aspect 95, wherein the catalyst comprises Cr—Zn, Cu—Zr, and/or Cu—Zn.

Aspect 97 provides the method of any one of Aspects 95-96, wherein the catalyst comprises a Cu—Zn catalyst.

Aspect 98 provides the method of any one of Aspects 95-97, wherein the forming the methanol comprises reacting the CO and the hydrogen in the presence of the catalyst at a temperature of 20° C. to 500° C.

Aspect 99 provides the method of any one of Aspects 95-98, wherein the forming the methanol comprises reacting the CO and the hydrogen in the presence of the catalyst at a temperature of 200° C. to 300° C.

Aspect 100 provides the method of any one of Aspects 95-99, wherein forming the methanol comprises reacting the CO and the hydrogen in the presence of the catalyst at a pressure of 0.1 MPa to 40 MPa.

Aspect 101 provides the method of any one of Aspects 95-100, wherein forming the methanol comprises reacting the CO and the hydrogen in the presence of the catalyst at a pressure of 3 MPa to 10 MPa.

Aspect 102 provides the method of any one of Aspects 94-101, wherein the method further comprises recycling at least some exothermic heat generated by the formation of the methanol from the syngas composition back into the method.

Aspect 103 provides a method of forming a syngas composition, the method comprising:
hydrolyzing $CaCl_2$ to form HCl and $Ca(OH)_2$;
reacting the HCl with $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$; and
electrolytically converting the $CO_2$ and the water into the syngas composition comprising carbon monoxide and hydrogen.

Aspect 104 provides the method of Aspect 103, further comprising reacting a used $CO_2$-capture sorbent with the $Ca(OH)_2$, to form the $CaCO_3$, wherein at least some of the $Ca(OH)_2$ formed in the hydrolysis of the $CaCl_2$ to form the HCl and the $Ca(OH)_2$ is recycled as at least some of the $Ca(OH)_2$ used in the reacting of the used $CO_2$-capture sorbent with the $Ca(OH)_2$.

Aspect 105 provides the method of any one of Aspects 103-104, further comprising reacting $Ca(HCO_3)_2$ from a water source (e.g., ocean water) with the $Ca(OH)_2$, to form the $CaCO_3$, wherein at least some of the $Ca(OH)_2$ formed in the hydrolysis of the $CaCl_2$ to form the HCl and the $Ca(OH)_2$ is recycled as at least some of the $Ca(OH)_2$ used in the reacting of the $Ca(HCO_3)_2$ with the $Ca(OH)_2$.

Aspect 106 provides a method of regenerating a used hydroxide-based $CO_2$-capture sorbent, the method comprising:
hydrolyzing a metal halide salt to form a hydrohalic acid and a hydroxide salt of the metal in the metal halide salt, the metal comprising an alkaline earth metal or an alkali metal;
reacting the used hydroxide-based $CO_2$-capture sorbent with the hydroxide salt, to form a carbonate salt of the metal in the metal halide salt;
reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt; and
electrolytically converting the $CO_2$ and the water into a syngas composition comprising carbon monoxide and hydrogen.

Aspect 107 provides a method of regenerating a used hydroxide-based $CO_2$-capture sorbent, the method comprising:
hydrolyzing $CaCl_2$ to form HCl and $Ca(OH)_2$;
reacting the used hydroxide-based $CO_2$-capture sorbent with the $Ca(OH)_2$, to form $CaCO_3$;
reacting the HCl with the $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$; and
electrolytically converting the $CO_2$ and the water into a syngas composition comprising carbon monoxide and hydrogen.

Aspect 108 provides a method of producing a syngas composition, the method comprising:
hydrolyzing a metal halide salt to form a hydrohalic acid and a hydroxide salt of the metal in the metal halide salt, the metal comprising an alkaline earth metal or an alkali metal;
reacting a bicarbonate salt from a water source comprising ocean water with the hydroxide salt, to form a carbonate salt of the metal in the metal halide salt;
reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt; and
electrolytically converting the $CO_2$ and the water into the syngas composition including carbon monoxide and hydrogen.

Aspect 109 provides a method of producing methanol, the method comprising:
hydrolyzing a metal halide salt to form a hydrohalic acid and a hydroxide salt of the metal in the metal halide salt, the metal comprising an alkaline earth metal or an alkali metal;
reacting a bicarbonate salt from a water source comprising ocean water with the hydroxide salt, to form a carbonate salt of the metal in the metal halide salt;
reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt;
electrolytically converting the $CO_2$ and the water into a syngas composition including carbon monoxide and hydrogen; and
reacting the carbon monoxide and the hydrogen in the presence of a catalyst to form the methanol.

Aspect 110 provides a method of producing a syngas composition, the method comprising:
hydrolyzing $CaCl_2$ to form HCl and $Ca(OH)_2$;
reacting $Ca(HCO_3)_2$ from a water source comprising ocean water with the $Ca(OH)_2$, to form $CaCO_3$; and
reacting the HCl with the $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$; and
electrolytically converting the $CO_2$ and the water into the syngas composition including carbon monoxide and hydrogen.

Aspect 111 provides a method of producing methanol, the method comprising:
hydrolyzing $CaCl_2$ to form HCl and $Ca(OH)_2$;
reacting $Ca(HCO_3)_2$ from a water source comprising ocean water with the $Ca(OH)_2$, to form $CaCO_3$; and
reacting the HCl with the $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$;
electrolytically converting the $CO_2$ and the water into a syngas composition including carbon monoxide and hydrogen; and
reacting the carbon monoxide and the hydrogen in the presence of a catalyst to form the methanol.

Aspect 112 provides the method of any one or any combination of Aspects 1-111 optionally configured such that all elements or options recited are available to use or select from.

What is claimed is:
1. A method of forming a syngas composition, the method comprising:
hydrolyzing a metal halide salt to form a hydrohalic acid and a hydroxide salt of the metal in the metal halide salt, the metal comprising an alkaline earth metal or an alkali metal;
reacting the hydrohalic acid with a metal carbonate salt, wherein the metal carbonate salt is a carbonate salt of the alkaline earth metal or alkali metal, to form $CO_2$, water, and the metal halide salt, wherein at least some of the metal halide salt formed from the reacting of the hydrohalic acid with the metal carbonate salt is recycled as at least some of the metal halide salt in the hydrolyzing of the metal halide salt to form the hydrohalic acid and the hydroxide salt; and electrolytically converting the $CO_2$ and the water into the syngas composition comprising carbon monoxide and hydrogen.

2. The method of claim 1, wherein:
the metal carbonate salt is $CaCO_3$,
the metal halide salt is $CaCl_2$,
the hydrohalic acid is HCl, and
the hydroxide salt is $Ca(OH)_2$.

3. The method of claim 2, wherein the $CaCO_3$ is produced from a $CO_2$-capture sorbent, is a $CaCO_3$ precipitate formed from water softening, is natural limestone, or a combination thereof.

4. The method of claim 1, wherein the hydrolyzing of the metal halide salt is performed at a pressure of 0.1 MPa to 9 MPa and at a temperature of 300° C. to 500° C., and wherein the reacting of the hydrohalic acid with the metal carbonate salt is performed at a pressure of 0.1 MPa to 9 MPa and at a temperature of room temperature to 500° C.

5. The method of claim 1, wherein the metal halide salt formed from the reacting of the hydrohalic acid with the metal carbonate salt is 80 wt % to 100 wt % of the metal halide salt used in the hydrolyzing of the metal halide salt to form the hydrohalic acid and the hydroxide salt.

6. The method of claim 1, further comprising reacting a bicarbonate salt from a natural water source, wherein the bicarbonate salt is $NaHCO_3$, $Mg(HCO_3)_2$, $Ca(HCO_3)_2$, $KHCO_3$, or a combination thereof, with the hydroxide salt to provide the metal carbonate salt, wherein the natural water source comprises salt water, ocean water, brackish water, fresh water, a stream, a pond, a lake, a river, or a combination thereof.

7. The method of claim 1, wherein the water formed during the reacting of the hydrohalic acid comprises gaseous water.

8. The method of claim 1, wherein the electrolytic conversion of the $CO_2$ and the water into the syngas composition converts 50% to 100% of the $CO_2$ and 50% to 100% of the water.

9. The method of claim 1, wherein carbon monoxide is 15 mol % to 40 mol % of the syngas composition, and wherein hydrogen is 30 mol % to 80 mol % of the syngas composition.

10. The method of claim 1, wherein the electrolytically converting the $CO_2$ and the water into the syngas composition comprises placing the $CO_2$ and/or the water into contact with an electrolytic cell, wherein the electrolytic cell comprises a reverse fuel cell, a solid oxide electrolysis cell or a molten carbonate electrolysis cell.

11. The method of claim 10, wherein the electrolytic cell comprises a solid oxide electrolysis cell.

12. The method of claim 11, wherein the electrolytic cell comprises an electrolyte comprising yttria-stabilized zirconia (YSZ), a cathode comprising Ni-YSZ, and an anode comprising lithium strontium manganite (LSM)-YSZ cathode.

13. The method of claim 10, wherein the method comprises using the electrolytic cell at a temperature of 500° C. to 1,000° C.

14. The method of claim 1, wherein the method further comprises using the syngas composition as a starting material to form a product comprising ammonia, methanol, a liquid fuel, a lubricant, gasoline, an oxo alcohol, or a combination thereof.

15. The method of claim 1, further comprising recycling at least some exothermic heat generated by the formation of the product from the starting material in the method, comprising supplying at least part of the generated exothermic heat to the reaction of the hydrohalic acid with the metal carbonate salt to form the metal halide salt.

16. The method of claim 1, wherein the method is a method of making methanol, wherein the method further comprises using the syngas composition as a starting material to form methanol, and wherein forming the methanol comprises reacting the CO and the hydrogen in the presence of a catalyst to form methanol.

17. The method of claim 16, wherein the catalyst comprises Cr—Zn, Cu—Zr, and/or Cu—Zn.

18. The method of claim 16, wherein the forming the methanol comprises reacting the CO and the hydrogen in the presence of the catalyst at a temperature of 20° C. to 500° C. and at a pressure of 0.1 MPa to 40 MPa.

19. A method of forming a syngas composition, the method comprising:
hydrolyzing $CaCl_2$ to form HCl and $Ca(OH)_2$;
reacting the HCl with $CaCO_3$, to form $CO_2$, water, and $CaCl_2$, wherein at least some of the $CaCl_2$ formed from the reacting of the HCl with the $CaCO_3$ is recycled as at least some of the $CaCl_2$ in the hydrolyzing of the $CaCl_2$ to form the HCl and the $Ca(OH)_2$; and
electrolytically converting the $CO_2$ and the water into the syngas composition comprising carbon monoxide and hydrogen.

20. A method of producing methanol, the method comprising:
hydrolyzing a metal halide salt to form a hydrohalic acid and a hydroxide salt of the metal in the metal halide salt, the metal comprising an alkaline earth metal or an alkali metal;
reacting a bicarbonate salt from a water source comprising ocean water with the hydroxide salt, to form a carbonate salt of the metal in the metal halide salt;
reacting the hydrohalic acid with the carbonate salt, to form $CO_2$, water, and the metal halide salt, wherein at least some of the metal halide salt formed from the reacting of the hydrohalic acid with the carbonate salt is recycled as at least some of the metal halide salt in the hydrolyzing of the metal halide salt to form the hydrohalic acid and the hydroxide salt;
electrolytically converting the $CO_2$ and the water into a syngas composition comprising carbon monoxide and hydrogen; and
reacting the carbon monoxide and the hydrogen in the presence of a catalyst to form the methanol.

* * * * *